(12) United States Patent
Conant et al.

(10) Patent No.: US 10,190,163 B2
(45) Date of Patent: Jan. 29, 2019

(54) SINGLE CELL NUCLEIC ACIDS FOR HIGH-THROUGHPUT STUDIES

(71) Applicant: Fluidigm Corporation, South San Francisco, CA (US)

(72) Inventors: Carolyn G. Conant, South San Francisco, CA (US); Tze Howe Charn, South San Francisco, CA (US); Jason A. A. West, Pleasanton, CA (US); Xiaohui Wang, South San Francisco, CA (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 226 days.

(21) Appl. No.: 15/055,252

(22) Filed: Feb. 26, 2016

(65) Prior Publication Data
US 2016/0251714 A1 Sep. 1, 2016

Related U.S. Application Data

(60) Provisional application No. 62/126,349, filed on Feb. 27, 2015.

(51) Int. Cl.
*C12Q 1/68* (2018.01)
*C12Q 1/6874* (2018.01)
*C12Q 1/6844* (2018.01)
*B01L 3/00* (2006.01)

(52) U.S. Cl.
CPC .......... *C12Q 1/6874* (2013.01); *B01L 3/5027* (2013.01); *C12Q 1/6844* (2013.01)

(58) Field of Classification Search
CPC ................ C12Q 1/6844; C12Q 1/6874; C12Q 2565/629
See application file for complete search history.

(56) References Cited

U.S. PATENT DOCUMENTS

| | | | |
|---|---|---|---|
| 8,450,063 B2 | 5/2013 | Dube et al. | |
| 8,628,923 B2 | 1/2014 | Hamilton et al. | |
| 8,691,509 B2 | 4/2014 | May et al. | |
| 8,697,363 B2 | 4/2014 | Mir et al. | |
| 9,074,204 B2 | 7/2015 | Anderson et al. | |
| 9,440,231 B2 | 9/2016 | West et al. | |
| 9,677,119 B2 | 6/2017 | May et al. | |
| 2009/0317798 A1 | 12/2009 | Heid et al. | |
| 2010/0120038 A1 | 5/2010 | Mir et al. | |
| 2010/0178655 A1 | 7/2010 | Hamilton et al. | |
| 2010/0203538 A1 | 8/2010 | Dube et al. | |
| 2010/0273219 A1 | 10/2010 | May et al. | |
| 2010/0285537 A1 | 11/2010 | Zimmermann | |
| 2011/0053806 A1 | 3/2011 | Amin | |
| 2011/0129841 A1 | 6/2011 | Heid et al. | |
| 2011/0143949 A1 | 6/2011 | Heid et al. | |
| 2013/0005585 A1 | 1/2013 | Anderson et al. | |
| 2013/0323732 A1 | 12/2013 | Anderson et al. | |
| 2014/0087973 A1 | 3/2014 | Amin | |
| 2014/0154679 A1 | 6/2014 | Dube et al. | |
| 2014/0186827 A1 | 7/2014 | Jones et al. | |
| 2014/0193812 A1 | 7/2014 | Hamilton et al. | |
| 2014/0227691 A1 | 8/2014 | May et al. | |
| 2014/0272952 A1 | 9/2014 | May et al. | |
| 2014/0296090 A1 | 10/2014 | Mir et al. | |
| 2015/0203887 A1* | 7/2015 | Lazinski | C12Q 1/6855 435/91.2 |
| 2016/0208322 A1 | 7/2016 | Anderson et al. | |
| 2016/0244742 A1 | 8/2016 | Linnarsson et al. | |
| 2016/0251714 A1 | 9/2016 | Conant et al. | |
| 2016/0340728 A1 | 11/2016 | Hamilton et al. | |
| 2017/0043340 A1 | 2/2017 | West et al. | |
| 2017/0175170 A1 | 6/2017 | Chen et al. | |

FOREIGN PATENT DOCUMENTS

| | | |
|---|---|---|
| WO | WO 2007/044091 A2 | 4/2007 |
| WO | WO 2010/117620 A2 | 10/2010 |
| WO | WO 2013/130714 A1 | 9/2013 |
| WO | WO 2013/177206 A2 | 11/2013 |
| WO | WO 2014/201273 A1 | 12/2014 |
| WO | WO 2016/138490 A1 | 9/2016 |

OTHER PUBLICATIONS

PCT International Search Report and Written Opinion dated Jul. 15, 2016 issued in PCT/US16/19952.
PCT International Preliminary Report on Patentability dated Aug. 29, 2017 issued in PCT/US16/19952.
Dominguez, et al., (2013) "Highly multiplexed quantitation of gene expression on single cells," *J. Immunological Methods* 391(0): 133-145 [NIH Public Access—Author Manuscript—24 pages].
Ooi, et al., (2015) "Unlocking Protein Expression in Single Cells Using the Fluidigm C1™ and Biomark™ Systems" *AGBT 2015: #71 Fluidigm poster*—One Page.
Wang, et al., (2014) "Clonal evolution in breast cancer revealed by single nucleus genome sequencing," *Nature* 512(7513):155-160 [15 pages]; doi:10.1038/nature13600.
EP Extended European Search Report dated Jun. 22, 2018 issued in EP 16756523.3.

(Continued)

*Primary Examiner* — David C Thomas
(74) *Attorney, Agent, or Firm* — Emily M. Haliday; Weaver Austin Villeneuve & Sampson LLP

(57) ABSTRACT

Described herein are cell-based analytic methods, including a method of incorporating nucleic acid sequences into reaction products from a cell population, wherein the nucleic acid sequences are incorporated into the reaction products of each cell individually or in small groups of cells individually. Also described herein is a matrix-type microfluidic device that permits at least two reagents to be delivered separately to each cell or group of cells, as well as primer combinations useful in the method and device.

56 Claims, 22 Drawing Sheets
(22 of 22 Drawing Sheet(s) Filed in Color)

(56) References Cited

OTHER PUBLICATIONS

Kurimoto, et al., (2006) "An improved single-cell cDNA amplification method for efficient high-density oligonucleotide microarray analysis," *Nucleic Acids Research* 34(5): e42 (17 pages) doi:10.1093/nar/gk1050.

Parameswaran, et al., (2007) "A pyrosequencing-tailored nucleotide barcode design unveils opportunities for large-scale sample multiplexing," *Nucleic Acids Research* 35(19): e130 (9 pages) doi:10.1093/nar/gkm760.

* cited by examiner

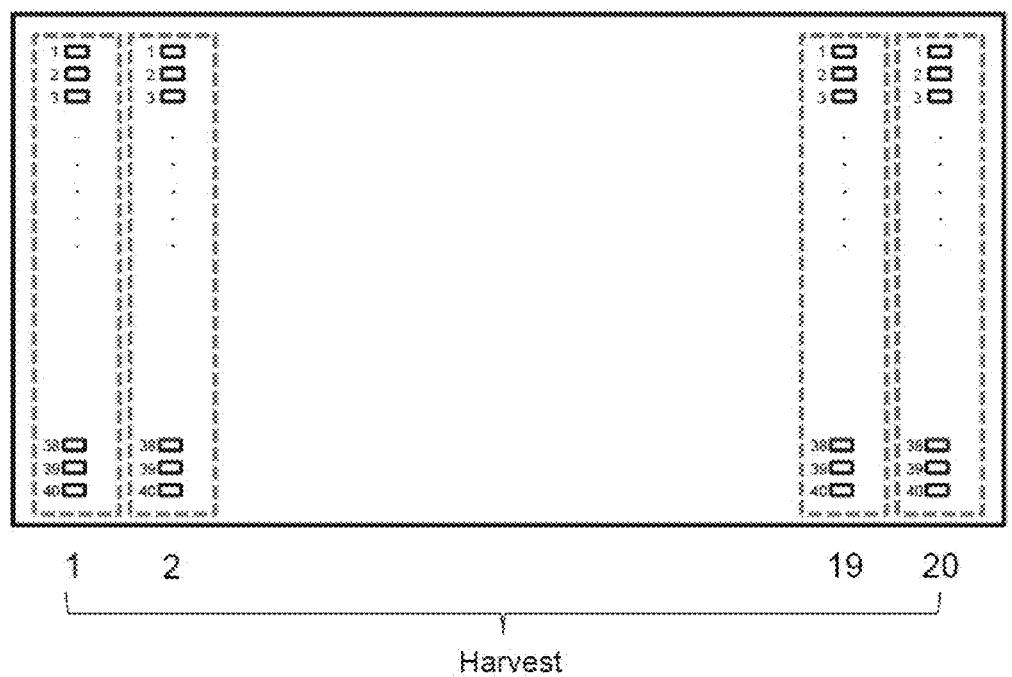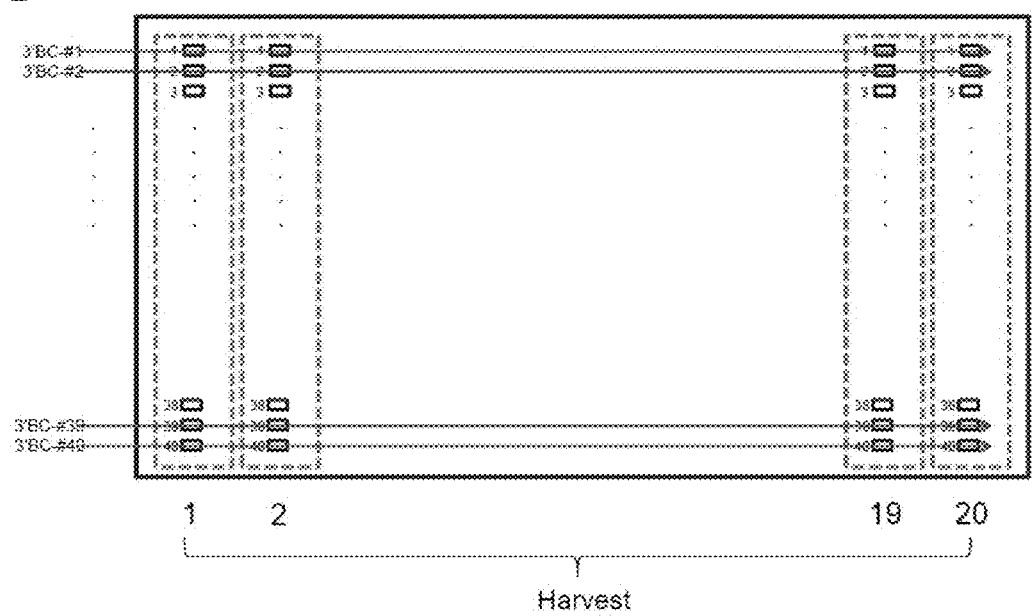
Figure 1A-B

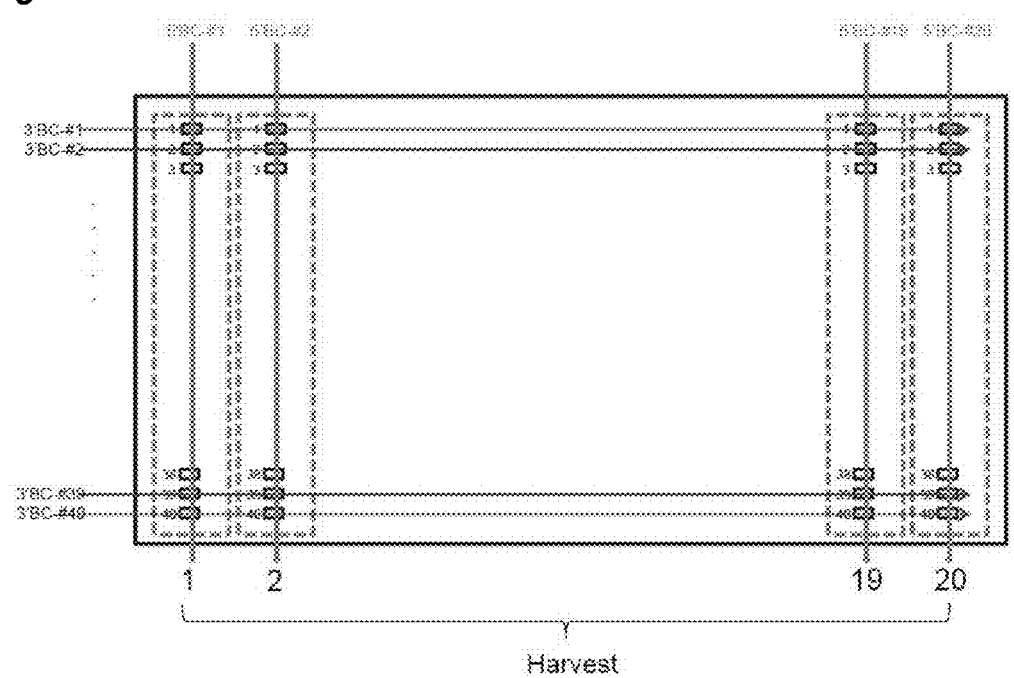
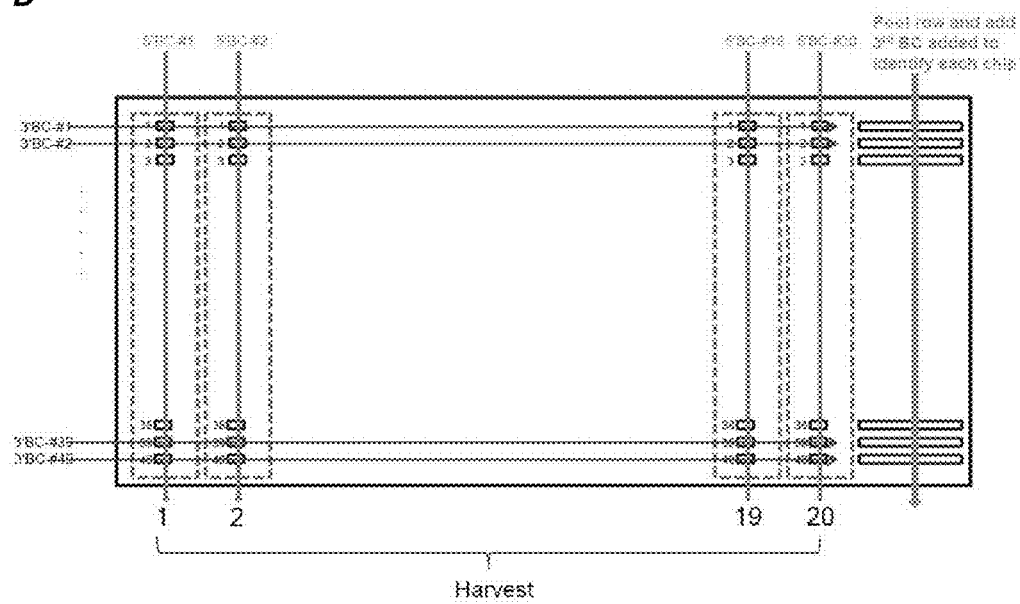
*Figure 1C-D*

A
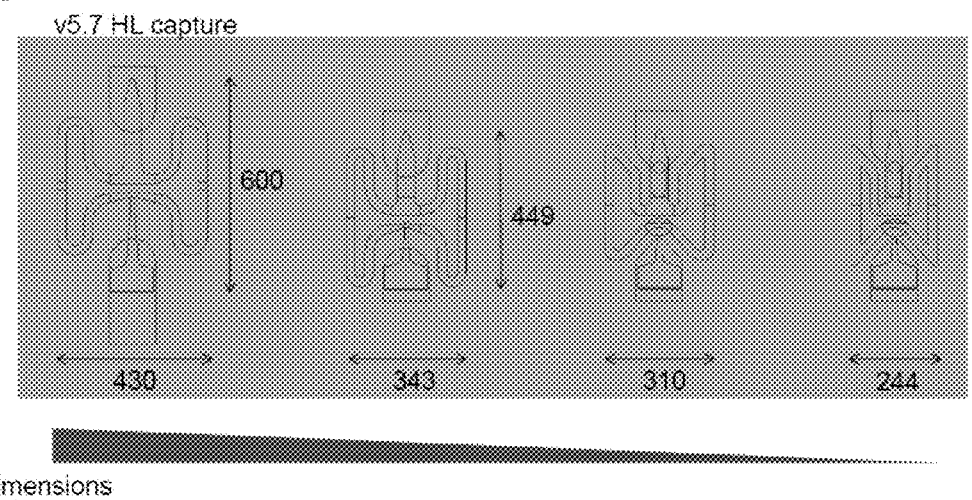
Dimensions
B
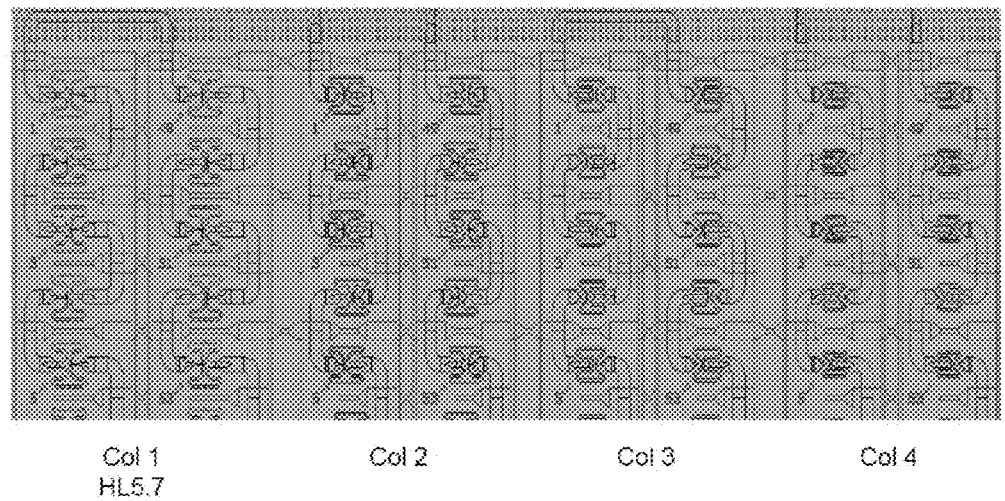
Col 1  Col 2  Col 3  Col 4
HL5.7
*Figure 4A-B*

C
Col 1
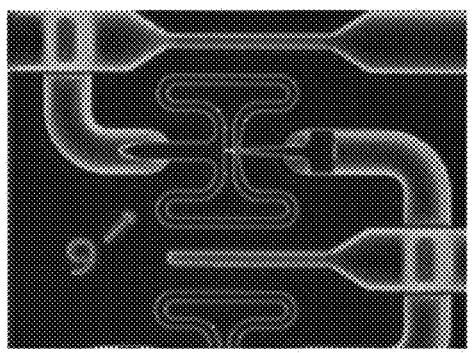
Col 2
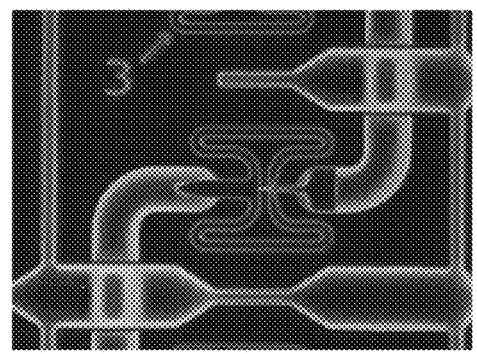
Col 3
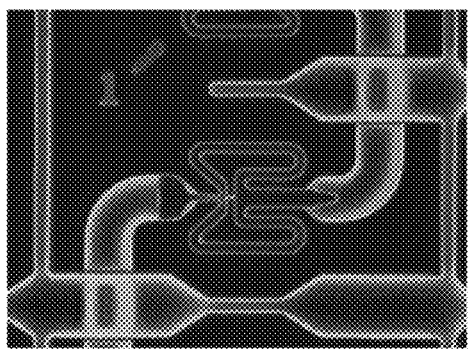
Col 4
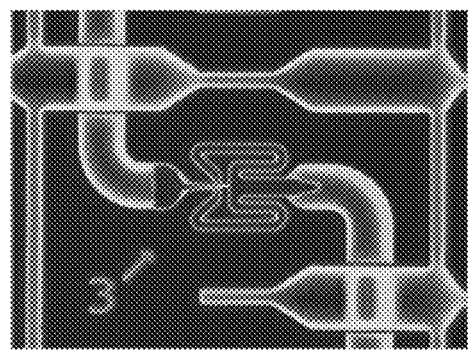
D
| | | | | | | |
|---|---|---|---|---|---|---|
| Col 1 | 22 | 68 | 6 | 0 | 0 | 71 |
| Col 2 | 23 | 68 | 4 | 1 | 0 | 71 |
| Col 3 | 13 | 72 | 8 | 1 | 2 | 75 |
| | | | | | | |
|---|---|---|---|---|---|---|
| Col 1 | 43 | 52 | 1 | 0 | 0 | 54 |
| Col 2 | 34 | 59 | 2 | 1 | 0 | 61 |
| Col 3 | 8 | 85 | 0 | 2 | 1 | 89 |
| Col 4 | 8 | 82 | 3 | 2 | 1 | 85 |
*Figure 4C-D*

Multiplex by ligation

⬇ Add Oligo #1 with BC2/Univ1 and a random or primer specific sequence

BC1
Univ1

⬇ Add Oligo #2 with BC2/Univ2

BC1
Univ1
BC2
Univ2

⬇ Ligation (may not be necessary)

BC1
Univ1
BC2
Univ2

*Figure 15*

Multiplex with multiple antibodies and PLA or PEA

SINGLE CELL NUCLEIC ACIDS FOR HIGH-THROUGHPUT STUDIES

CROSS-REFERENCE TO RELATED APPLICATIONS

This application claims the benefit of U.S. provisional application No. 62/126,349, filed Feb. 27, 2015, which is hereby incorporated by reference in its entirety.

STATEMENT AS TO RIGHTS TO INVENTIONS MADE UNDER FEDERALLY SPONSORED RESEARCH AND DEVELOPMENT

Not applicable.

FIELD

The subject matter disclosed herein relates to generally to the area of analysis of single cells or small groups of cells. In particular, the subject matter relates to methods and compositions for performing separate reactions with at least two reagents independently added to multiple cells or groups of cells (or the components thereof), optionally followed by further analysis.

BACKGROUND

There is an interest in the life sciences in the quantitation of transcription in substantial numbers of single cells in one study. At present, Fluidigm Corporation enables the study of transcription from 96 single cells at a time through the C1™ system "integrated fluidic circuit" (IFC™) microfluidic devices.

Currently available chemistries from commercial sources used to prepare cDNA from single cells for analysis of mRNA transcript levels, usually but not limited to mRNA sequencing, cannot be used in a Fluidigm IFC™ unless there is an addressable outlet well for each single cell. There is no easy way to identify the transcripts from single cells using the commercial kits when the cDNA from each cell is combined together in a pool; this is necessary in Fluidigm IFCs™ developed for more than 96 single cells on the Generation 2 carrier since there are not enough wells to output each discrete single-cell cDNA sample.

If the cDNA is to be sequenced, e.g., using the bridge amplification (cluster generation) and sequencing method commercialized by Illumina, Inc. (San Diego, Calif.), a further problem is the need for individual commercial tagmentation reactions for each cell's cDNA from the 96-cell IFC™ to allow for controlled fragmentation for flow cell clustering and sample identification during sequencing.

SUMMARY

This disclosure includes the development of a high throughput (HT) capture architecture in an IFC as well as companion chemistry, which facilitates convenient single cell transcriptome amplification and identification of specific transcripts from each cell and has a variety of other applications as well.

In various aspects, the disclosure(s) contemplated herein may include, but need not be limited to, any one or more of the following embodiments:

Embodiment 1: A method of exposing cells from a population to at least two different reagents, wherein each cell is exposed to the reagents individually, or in groups of two of more, the method including:

(a) distributing cells from the population to a plurality of capture sites in a microfluidic device so that a plurality of capture sites each includes one or more cells;

(b) providing one or more first reagent(s) to each capture site;

(c) providing one or more second reagent(s) to each capture site, wherein the second reagent(s) is/are different from the first reagent(s) and is/are provided separately from the first reagent(s);

(d) conducting a reaction, whereby the reaction products encode an item of capture site information;

(e) recovering the reaction products; and (f) analyzing the reaction products, wherein such analysis permits the identification of particular reaction products as having been derived from a single cell or group of cells at a particular capture site.

Embodiment 2: A method of incorporating nucleic acid sequences into reaction products from a cell population, wherein the nucleic acid sequences are incorporated into the reaction products of each cell individually, or in groups of up to 1000, the method including:

(a) distributing cells from the population to a plurality of capture sites in a microfluidic device so that a plurality of capture sites each includes one or more cells;

(b) providing one or more first reagent(s) to each capture site;

(c) providing one or more second reagent(s) to each capture site, wherein the second reagent(s) is/are different from the first reagent(s) and is/are provided separately from the first reagent(s);

(d) conducting a reaction in which nucleic acid sequences are incorporated into the reaction products of each cell or group of cells, individually;

(e) recovering the reaction products; and (f) analyzing the reaction products, wherein such analysis permits the identification of particular reaction products as having been derived from a single cell or group of cells at a particular capture site.

Embodiment 3: A method of incorporating nucleic acid sequences into nucleic acids of a cell population, wherein the nucleic acid sequences are incorporated into the nucleic acids of each cell individually or in groups of up to 1000, the method including:

(a) distributing cells from the population to a plurality of capture sites in a microfluidic device so that a plurality of capture sites each includes one or more cells;

(b) providing one or more first reagent(s) to each capture site;

(c) providing one or more second reagent(s) to each capture site, wherein the second reagent(s) is/are different from the first reagent(s) and is/are provided separately from the first reagent(s);

(d) conducting a reaction in which nucleic acid sequences are incorporated into the nucleic acids of each cell or group of cells, individually, to produce reaction products;

(e) recovering the reaction products; and (f) analyzing the reaction products, wherein such analysis permits the identification of particular reaction products as having been derived from a single cell or group of cells at a particular capture site.

Embodiment 4: The method of embodiment any preceding embodiments, where the distribution is carried out so that a plurality of capture sites each comprise not more than a single cell.

Embodiment 5: The method of any preceding embodiment, wherein the reaction incorporates a nucleotide barcode into the reaction products.

Embodiment 6: The method of embodiment 5, wherein the barcode encodes an item of capture site information.

Embodiment 7: The method of any preceding embodiment, wherein the reaction incorporates a nucleic acid sequence that uniquely identifies the molecule into which it is incorporated (UMI).

Embodiment 8: The method of embodiment 3, wherein the reaction includes reverse transcription of RNA.

Embodiment 9: The method of embodiment 8, wherein the first reagent(s) comprise a reverse transcription (RT) primer including a poly-dT sequence and a first barcode 5' of the poly-dT sequence.

Embodiment 10: The method of embodiment 9, wherein the RT primer additionally includes a first UMI.

Embodiment 11: The method of embodiment 10, wherein the first UMI is 5' of the poly-dT sequence.

Embodiment 12: The method of embodiments 9-11, wherein the RT primer additionally includes a first linker.

Embodiment 13: The method of embodiment 12, wherein the first linker is at the 5' end of the RT primer.

Embodiment 14: The method of embodiments 9-13, wherein the RT primer additionally includes an anchor sequence 3' of the poly-dT sequence.

Embodiment 15: The method of embodiments 8-14, wherein the reaction additionally includes second-strand synthesis to produce cDNA.

Embodiment 16: The method of embodiments 8-15 wherein the second reagent(s) comprise a 5' oligonucleotide including a poly-riboG sequence.

Embodiment 17: The method of embodiment 15, wherein the 5' oligonucleotide includes a second barcode 5' of the poly-riboG sequence.

Embodiment 18: The method of embodiments 15 or 17, wherein the 5' oligonucleotide additionally includes a second UMI.

Embodiment 19: The method of embodiment 18, wherein the second UMI is 5' of the poly-riboG sequence.

Embodiment 20: The method of 15-19, wherein the 5' oligonucleotide additionally includes a second linker.

Embodiment 21: The method of embodiment 20, wherein the second linker is at the 5' end of the 5' oligonucleotide.

Embodiment 22: The method of embodiment 21, wherein the method includes producing cDNA, wherein one strand has the structure: 5'-second linker-nucleotide sequence derived from RNA-first linker-3', with a barcode located in between the linkers.

Embodiment 23: The method of embodiment 22, wherein the first barcode is located adjacent to the first linker.

Embodiment 24: The method of embodiment 23, wherein the second barcode is located adjacent to the second linker.

Embodiment 25: The method of embodiment 23, wherein said one strand of cDNA has the structure: 3'-second linker-poly dC-nucleotide sequence derived from RNA-first barcode-first linker-5'.

Embodiment 26: The method of embodiment 25, wherein said one strand of cDNA has the structure: 3'-second linker-second barcode-poly dC-nucleotide sequence derived from RNA-first barcode-first linker-5'.

Embodiment 27: The method of embodiment 25, wherein said one strand of cDNA has a structure selected from the group consisting of: 3'-second linker-poly dC-nucleotide sequence derived from RNA-first UMI-first barcode-first linker-5'; and 3'-second linker-poly dC-nucleotide sequence derived from RNA-first barcode-first UMI-first linker-5'.

Embodiment 28: The method of embodiments 27, wherein said one strand of cDNA has a structure selected from the group consisting of: 3'-second linker-second barcode-second UMI-poly dC-nucleotide sequence derived from RNA-first UMI-first barcode-first linker-5'; 3'-second linker-second barcode-second UMI-poly dC-nucleotide sequence derived from RNA-first barcode-first UMI-first linker-5'; 3'-second linker-second UMI-second barcode-poly dC-nucleotide sequence derived from RNA-first UMI-first barcode-first linker-5'; and 3'-second linker-second UMI-second barcode-poly dC-nucleotide sequence derived from RNA-first barcode-first UMI-first linker-5'.

Embodiment 29: The method of embodiment 3, wherein the reaction includes amplification of DNA.

Embodiment 30: The method of embodiment 29, wherein the first and/or second reagent(s) comprise first and/or second amplification primers, respectively, wherein the first and/or second amplification primers comprise a first or second barcode, respectively, that is 5' of a primer sequence.

Embodiment 31: The method of embodiment 30, wherein the first and/or second amplification primers additionally comprise a first or second UMI, respectively.

Embodiment 32: The method of embodiment 31, wherein the first or second UMI is 5' of the primer sequence.

Embodiment 33: The method embodiments 30-32, wherein the first and/or second amplification primer additionally includes a first or second linker.

Embodiment 34: The method of embodiment 33, wherein the first or second linker is at the 5' end of the amplification primer.

Embodiment 35: The method of embodiment 34, wherein the method includes producing amplicons, wherein one strand has the structure: 5'-second linker-nucleotide sequence derived from cellular DNA-first linker-3', with a barcode located in between the linkers.

Embodiment 36: The method of embodiment 35, wherein one strand has the structure: 3'-second linker-nucleotide sequence derived from cellular DNA-first barcode-first linker-5'.

Embodiment 37: The method of embodiment 25, wherein said one strand has the structure: 3'-second linker-second barcode-nucleotide sequence derived from cellular DNA-first barcode-first linker-5'.

Embodiment 38: The method of embodiment 25, wherein said one strand has a structure selected from the group consisting of: 3'-second linker-nucleotide sequence derived from cellular DNA-first UMI-first barcode-first linker-5'; and 3'-second linker-nucleotide sequence derived from cellular DNA-first barcode-first UMI-first linker-5'.

Embodiment 39: The method of embodiments 27, wherein said one strand has a structure selected from the group consisting of: 3'-second linker-second barcode-second UMI-nucleotide sequence derived from cellular DNA-first UMI-first barcode-first linker-5'; 3'-second linker-second barcode-second UMI-nucleotide sequence derived from cellular DNA-first barcode-first UMI-first linker-5'; 3'-second linker-second UMI-second barcode-nucleotide sequence derived from cellular DNA-first UMI-first barcode-first linker-5'; and 3'-second linker-second UMI-second barcode-poly dC-nucleotide sequence derived from cellular DNA-first barcode-first UMI-first linker-5'.

Embodiment 40: The method of any preceding embodiment, wherein the microfluidic device includes a matrix-type microfluidic device including: capture sites arranged in a matrix of R rows and C columns, wherein R and C are integers greater than 1, and wherein the capture sites can be fluidically isolated from one another after distribution of cells to the capture sites; a set of R first input lines configured to deliver the first reagent(s) to capture sites in a particular row; a set of C second input lines configured to deliver second reagent(s) to capture sites in a particular column, wherein said delivery is separate from the delivery first reagent(s), wherein, after the reaction, reaction products are recovered from the microfluidic device in pools of reaction products from individual rows or columns.

Embodiment 41: The method of embodiment 40, wherein an RT primer is delivered to capture sites via one set of the input lines, and a 5' oligonucleotide is delivered to the capture sites via the other set of input lines.

Embodiment 42: The method of embodiment 40, wherein a first amplification primer is delivered to capture sites via one set of the input lines, and a second amplification primer is delivered to the capture sites via the other set of input lines.

Embodiment 43: The method of any preceding embodiment, wherein all methods steps are performed in the microfluidic device.

Embodiment 44: The method of any of the preceding embodiments, wherein the reaction products are subjected to preamplification using linker primers that anneal to the first and second linkers, wherein the linker primers are the same or different.

Embodiment 45: The method of embodiment 44, wherein said preamplification is performed in the microfluidic device.

Embodiment 46: The method of any of the preceding embodiments, wherein the reaction products are subjected to tagmentation.

Embodiment 47: The method of any preceding embodiment, wherein the reaction incorporates one or more DNA sequencing primer binding sites into the reaction products.

Embodiment 48: The method of any of the preceding embodiments, wherein the reaction products are subjected to DNA sequencing.

Embodiment 49: The method of embodiment 48, wherein the sequences obtained from DNA sequencing are identified as having been derived from a particular capture site based on one or two barcodes.

Embodiment 50: The method of any of embodiments 40-49, wherein the exported pools are separately subjected to one or more of the steps of embodiments 44-49.

Embodiment 51: The method of any of embodiments 40-49, wherein the exported pools are combined into one reaction mixture, which is subjected to one or more of the steps of embodiments 44-49.

Embodiment 52: The method of any of embodiments 40-51, wherein the microfluidic device is sufficiently transparent on at least one surface to permit visualization of cells and/or, when a visualizable label is employed, signals associated with cells or reaction products.

Embodiment 53: The method of embodiment 52, additionally including imaging the cell-occupied capture sites before conducting the reaction.

Embodiment 54: The method of any preceding embodiment, wherein the reaction includes whole transcriptome amplification (WTA), whole genome amplification (WGA), protein proximity ligation, microRNA (mRNA) preamplification, target-specific amplification of RNA or DNA.

Embodiment 55: The method of any preceding embodiment, wherein the microfluidic device includes at least 750 capture sites.

Embodiment 56: A matrix-type microfluidic device including:

a plurality of capture sites arranged in a matrix of R rows and C columns, wherein R and C are integers greater than 1, and wherein:

each capture site includes a capture feature that captures one or more cells;

the capture sites can be fluidically isolated from one another after distribution of cells to the capture sites;

a set of R first input lines configured to deliver the first reagent(s) to capture sites in a particular row; and a set of C second input lines configured to deliver second reagent(s) to capture sites in a particular column, wherein said delivery is separate from the delivery first reagent(s).

Embodiment 57: The device of embodiment 56, wherein the capture feature is configured to capture not more than a single cell.

Embodiment 58: The device of embodiments 56 or 57, wherein the microfluidic device is sufficiently transparent on at least one surface to permit visualization of cells and/or, when a visualizable label is employed, signals associated with cells or reaction products.

Embodiment 59: The device embodiments 56-58, wherein each capture site includes four chambers that can be fluidically isolated from one another, wherein one of said chambers includes the capture feature.

Embodiment 60: A method of operating the microfluidic device of embodiments 56-59, wherein the method includes:

(a) distributing cells from a population of cells to the capture sites so that a plurality of capture sites comprise one or more cells;

(b) after distribution, fluidically isolating the capture sites from one another;

(c) providing one or more first reagent(s) to each fluidically isolated capture site via the R first input lines;

(d) providing one or more second reagent(s) to each fluidically isolated capture site via the C second input lines, wherein the second reagent(s) is/are different from the first reagent(s); and (e) conducting a reaction.

Embodiment 61: The method of embodiment 60, wherein a plurality of capture sites comprise not more than a single cell.

Embodiment 62: The method of embodiments 60 or 61, additionally including recovering the reaction products as a pool of reaction products from each row or as a pool of reaction products from each column.

Embodiment 63: The method of embodiments 60-62, wherein said recovering includes providing a harvesting reagent to the R first input lines or the C second input lines.

Embodiment 64: A primer combination for use in producing cDNA from RNA, the combination including:

(a) a reverse transcription (RT) primer including an anchor sequence, a poly-dT sequence 5' of the anchor sequence, a first barcode 5' of the poly-dT sequence, and a first linker 5' of the first barcode sequence; and (b) a 5' oligonucleotide including a poly-riboG sequence, a second barcode 5' of the poly-riboG sequence, and a second linker 5' of the second barcode.

Embodiment 65: The primer combination of embodiment 64, wherein one or both primers comprise a UMI.

Embodiment 66: A primer combination for use in amplifying DNA, the combination including first and second amplification primers that can prime the production of an amplicon in the presence of suitable template DNA, wherein each amplification primer includes: a primer sequence; a barcode that is 5' of the primer sequence, wherein the barcodes in each primer are different; and a linker that is 5' of the barcode; wherein one or both primers also comprise a UMI that is 5' of the primer sequence and 3' of the linker.

Embodiment 67: The primer combination of embodiments 64-66, additionally including one or more linker primer(s) that anneal(s) to the linkers.

Embodiment 68: The primer combination of embodiments 64-67, wherein the linker primers comprise a 5' linker primer and a different 3' linker primer.

Embodiment 69: The primer combination of embodiments 68, additionally including a primer including a portion specific for the 3' linker primer or its complement and/or a primer including a portion specific for the 5' linker primer or its complement, wherein the primer(s) additionally comprise a flow cell sequence useful in cluster generation in bridge sequencing.

Embodiment 70: A method of producing cDNA from RNA, wherein the primer combination of embodiments 64 or 65 is employed for first-strand synthesis.

Embodiment 71: A method of amplifying DNA, the method including contacting template DNA with the primer combination of embodiment 66 to produce amplicons.

Embodiment 72: A method of preamplifying the cDNA or amplicons of embodiments 70 or 71, respectively, the method including preamplifying the cDNA or amplicons with the linker primers of embodiments 67 and 68.

Embodiment 73: A method of cluster generation in bridge sequencing of cDNA or amplicons produced in embodiments 70-72, the method conducting cluster generation using the primer of embodiment 69.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-D: An illustrative matrix-type microfluidic device is shown schematically in (A). (B) illustrates the delivery of R different barcodes through the R different first input lines to the capture sites. (C) illustrates the delivery of C different barcodes through C different input lines to the capture sites. (D) illustrates that, after the reaction has been carried out, reaction products can be harvested for each column as a pool, for example, by applying a harvesting fluid to the C second input lines to push the reaction products out of outlets at one end of the input lines.

FIG. 4A-E: (A) shows a series of increasingly more miniaturized illustrative capture features, which facilitate the analysis of more cells per microfluidic device. (B) shows the arrangement of capture features in rows and columns, together with the channels for distributing cells to the capture features. (C) shows photomicrographs of the miniaturized capture features. (D) reports the cell occupancy data for two different capture site designs, with the top panel of the table showing the results for the miniaturized features, and the bottom panel of the table showing the results for illustrative double grooves capture features with different height ratios for top and bottom grooves. The first column in the table reports the number of capture features having no cells, and the second column reports the number of capture features having just 1 cell. (E) shows a schematic of an IFC having two different capture site designs: one having reduced dimensions and one having different height ratios for top and bottom grooves.

FIG. 15: An illustrative scheme for combinatorial barcoding of nucleic acid by ligation (BC1+2=two different barcodes; Univ1 and Univ2=universal primer binding sites, which can be the same or different).

DETAILED DESCRIPTION

Figure 2:
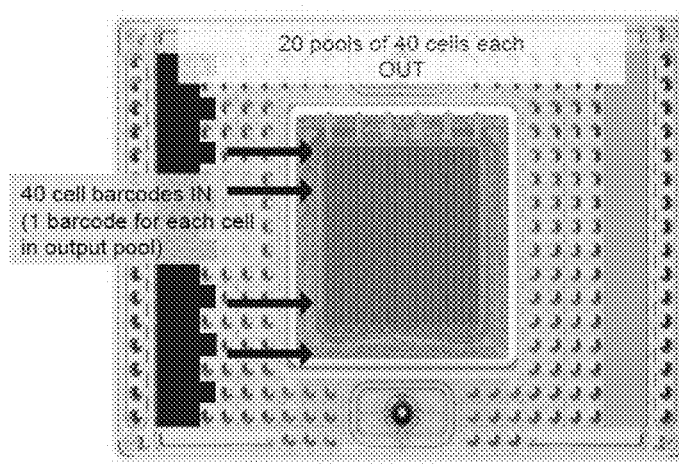
FIG. 2: A photograph of the illustrative matrix-type microfluidic device shown schematically in FIG. 1.

Described herein is a hygienic barcoding strategy on a HT IFC™ to allow for pooling of cDNA from many single cells (or small numbers of cells) post-IFC™ where the cells can be de-multiplexed from one another using cell-specific barcodes on each molecule following analysis of the transcripts. This strategy can be designed to facilitate simple barcode enrichment by amplification so that the majority of material queried will be barcoded rather than cDNA material that cannot be attributed to a particular cell, leading to generation of unusable sequence data.

Other barcoded cDNA enrichment strategies for single cells involve custom-made transposons and biotin-strepavidin-pulldowns increasing the workflow complexity of the enrichment while at the same time potentially reducing the amount of material available for sequencing due to the nature of this type of cleanup. The amplification-based barcode enrichment strategy enables single tagmentation reactions for large numbers of cells instead of one cell at a time without pulldowns or extra cleanup steps and without the need for generation of custom transposons.

Also described herein is an IFC™ architecture that enables the processing of discreetly captured or isolated single cells (or groups of cells) in combination with any multistep biochemical process that facilitates the analysis of intracellular macromolecules. Such process include, but are not limited to, Whole Genome amplification (WGA) for DNA sequencing, multiplexed protein proximity ligation assays to quantitate specific proteins, multiplexed microRNA preamplication, target-specific amplification of RNA transcripts or DNA sequences (e.g., genotyping polymorphic markers, such as SNPs, or otherwise analyzing genetic variations, such as copy number variations), targeted resequencing, or any combination thereof. In addition using the novel IFC™ architecture, simple modifications to the IFC™-associated control scripts enable the real-time detection of transcripts of single cells, which can be used in combination, for example, a controller that enables integrated thermal and pneumatic control, with optical detection of all unit cells in tandem. This combination provides the ability to link phenotype with gene expression analysis, while eliminating the lengthy and undesirable off-instrument imaging steps. This architecture can also be exploited to culture discreetly captured/isolated cells or groups of cells under any desired conditions, which can be modified on-chip by adding components such as, e.g., agonists or antagonists for particular receptors.

DEFINITIONS

Terms used in the claims and specification are defined as set forth below unless otherwise specified. These terms are defined specifically for clarity, but all of the definitions are consistent with how a skilled artisan would understand these terms.

As used herein, the term "microfluidic device" refers to any device that includes chambers and/or channels wherein at least one dimension is less than 1 millimeter. In certain embodiments, a microfluidic device includes fluid flow channels (or lines) and separate control channels (or lines) that function to control or regulate flow through the fluid channels.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "template" is used herein to refer to a nucleic acid molecule that serves as a template for a polymerase to synthesize a complementary nucleic acid molecule.

There term "template nucleic acids" is a generic term that encompasses "target nucleic acids."

The term "target nucleic acids" is used herein to refer to particular nucleic acids to be detected in the methods described herein. Accordingly, amplification of single nucleotide polymorphisms (SNPs), for example, is an example of target-specific amplification, whereas whole genome amplification is an example of the amplification that aims to amplify all template nucleic acids in the genome.

As used herein, the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. A first nucleotide sequence is said to be the "complement" of a second sequence if the first nucleotide sequence is complementary to the second nucleotide sequence. A first nucleotide sequence is said to be the "reverse complement" of a second sequence, if the first nucleotide sequence is complementary to a sequence that is the reverse (i.e., the order of the nucleotides is reversed) of the second sequence.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% G+C)$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

Figure 16:
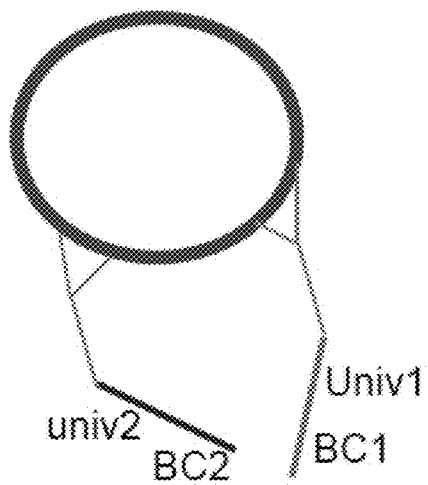
FIG. 16: An illustrative scheme for using combinatorial barcoding in protein proximity ligation (PLA) or extension (PEA; BC1+2=two different barcodes; Univ1 and Univ2=universal primer binding sites, which can be the same or different).
Figure 17:
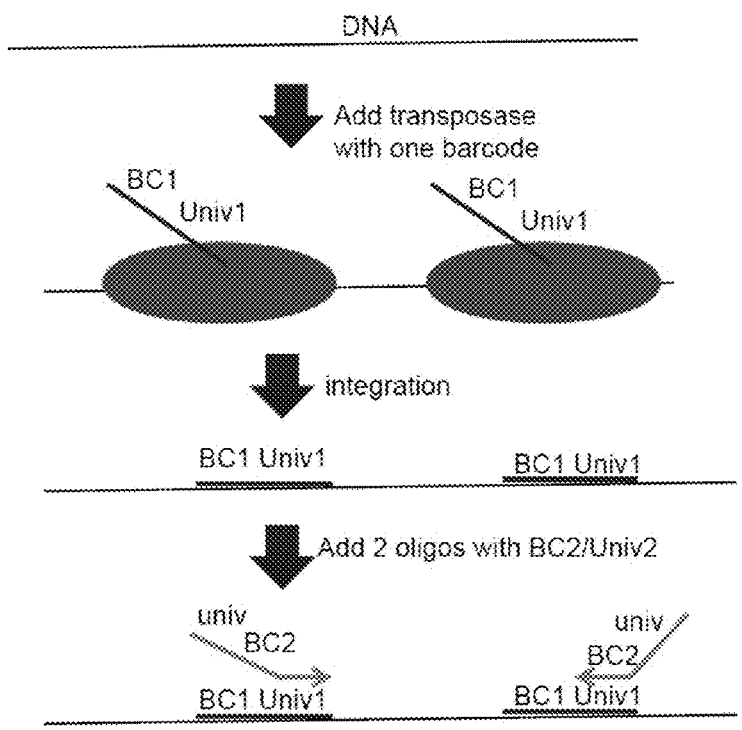
FIG. 17: An illustrative scheme for combinatorial barcoding using an enzyme, such as a transposase, to introduce the barcodes (BC1+2=two different barcodes; Univ1 and Univ2=universal primer binding sites, which can be the same or different).

As used herein the terms "nucleotide barcode" and "barcode" refer to a specific nucleotide sequence that encodes information about cDNA produced when a barcoded primer or oligonucleotide is employed in reverse transcription or the amplicon produced when one or more barcoded primer(s) is/are employed in an amplification reaction. As shown in FIGS. 16 and 17, barcodes may also be added to nucleotide sequences by other means, such as by ligation or via transposases.

In some embodiments, the barcode encodes "an item of capture site information." For example, for reactions carried out on a matrix-type microfluidic device, a barcode can encode the row or column of a capture site. Two barcodes, one encoding the row in which the barcode is introduced and the other encoding the column in which that barcode is introduced can define the specific capture site residing at the intersection of the row and column identified by the barcodes.

As used herein, "UMI" is an acronym for "unique molecular index," also referred to as "molecular index." A UMI is one in a group of indexes in which each index (or barcode) has an index sequence that is different from any of the other indexes in the group. One way to achieve this "uniqueness" is to use a string of nucleotides. For example, if the length of this string is 10 bases, there are more than 1 million unique sequences; if it is 20 bases long, there will be $10^{12}$ unique sequences. See Hug and Schulernz, "Measurement of the Number of Molecules of a Single mRNA Species in a Complex mRNA Preparation," J. Theor. Biol. (2003) 221, 615-624 and Hollas and Schuler, "A Stochastic Approach to Count RNA Molecules Using DNA Sequencing Methods" in Algorithms in Bioinformatics (2003): Third International Workshop, WABI 2003, Budapest, Hungary, Sep. 15-20, 2003, Series title: Lecture Notes in Computer Science Volume 2812, pp 55-62 (eds. Benson and Page).

A "linker" can, but need not, be or include a nucleic acid. Nucleotide linkers can be added to either end of a nucleotide sequence to be amplified to facilitate unbiased amplification using primers specific for the nucleotide linkers, which can be the same or different.

As used herein, an "anchor sequence" refers to a sequence in an oligonucleotide that serves to lock onto a target sequence, typically following a stretch of identical nucleotide bases. It usually occurs on the 3' end of the oligonucleotide, but is not limited to this position. It can consist of random nucleotides, often excluding the nucleotides from the stretch. For example, an illustrative anchor sequence that follows a poly-dT stretch in a primer (or oligonucleotide) might consist of a first position or portion containing any or all of the bases A, G, and/or C, but not T. The second position or portion might contain any combination of bases or all of the bases (A, G, T, C) on the terminus of the primer or oligonucleotide.

The term "adjacent," when used herein to refer two nucleotide sequences in a nucleic acid, can refer to nucleotide sequences that are separated by 1 to about 50 nucleotides, more specifically, by a range of about 1 to about 20 nucleotides, even more specifically, by a range of about 1 to about 10 nucleotides, or to sequences that directly abut one another (separated by 0 nucleotides).

As used herein with reference to a portion of a primer, the term "target-specific" nucleotide sequence refers to a sequence that can specifically anneal to a target nucleic acid or a target nucleotide sequence under suitable annealing conditions. Portions of primers can be "specific" in the same sense for nucleotide sequences other than targets.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 Feb.; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

"Whole transcriptome amplification" ("WTA") refers to any amplification method that aims to produce an amplification product that is representative of a population of RNA from the cell from which it was prepared. An illustrative WTA method entails production of cDNA bearing linkers on either end that facilitate unbiased amplification. In many implementations, WTA is carried out to analyze messenger (poly-A) RNA (this is also referred to as "RNAseq").

"Whole genome amplification" ("WGA") refers to any amplification method that aims to produce an amplification product that is representative of the genome from which it was amplified. Illustrative WGA methods include Primer extension PCR (PEP) and improved PEP (I-PEP), Degenerated oligonucleotide primed PCR (DOP-PCR), Ligation-mediated PCR (LMP), T7-based linear amplification of DNA (TLAD), Multiple displacement amplification (MDA).

The term "substantially" as used herein with reference to a parameter means that the parameter is sufficient to provide a useful result. Thus, "substantially complementary," as applied to nucleic acid sequences generally means sufficiently complementary to work in the described context. Typically, substantially complementary means sufficiently complementary to hybridize under the conditions employed.

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, nucleotides, oligonucleotides, labels, dyes, nucleases, and the like. Reagents for enzyme reactions include, for example, substrates, cofactors, buffer, metal ions, inhibitors, and activators. The term reagent also encompasses any component that influences cell growth or behavior, such as, e.g., buffer, culture medium or components thereof, agonists or antagonists, etc.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "stain", as used herein, generally refers to any organic or inorganic molecule that binds to a component to facilitate detection of that component.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

As use herein, the term "variation" is used to refer to any difference. A variation can refer to a difference between individuals or populations. A variation encompasses a difference from a common or normal situation. Thus, a "copy number variation" or "mutation" can refer to a difference from a common or normal copy number or nucleotide sequence. An "expression level variation" or "splice variant" can refer to an expression level or RNA or protein that differs from the common or normal expression level or RNA or protein for a particular, cell or tissue, developmental stage, condition, etc.

A "polymorphic marker" or "polymorphic site" is a locus at which nucleotide sequence divergence occurs. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

As used herein with respect to reactions, reaction mixtures, reaction volumes, etc., the term "separate" refers to reactions, reaction mixtures, reaction volumes, etc., where reactions are carried out in isolation from other reactions. Separate reactions, reaction mixtures, reaction volumes, etc. include those carried out in droplets (See, e.g., U.S. Pat. No. 7,294,503, issued Nov. 13, 2007 to Quake et al., entitled "Microfabricated crossflow devices and methods," which is incorporated herein by reference in its entirety and specifically for its description of devices and methods for forming and analyzing droplets; U.S. Patent Publication No. 20100022414, published Jan. 28, 2010, by Link et al., entitled "Droplet libraries," which is incorporated herein by reference in its entirety and specifically for its description of devices and methods for forming and analyzing droplets; and U.S. Patent Publication No. 20110000560, published Jan. 6, 2011, by Miller et al., entitled "Manipulation of Microfluidic Droplets," which is incorporated herein by reference in its entirety and specifically for its description of devices and methods for forming and analyzing droplets.), which may, but need not, be in an emulsion, as well as those wherein reactions, reaction mixtures, reaction volumes, etc. are separated by mechanical barriers, e.g., separate vessels, separate wells of a microtiter plate, or separate compartments of a matrix-type microfluidic device.

The term "fluidically isolated" is used herein to refer to state in which two or more elements of a microfluidic device are not in fluid communication with one another.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

Cell-Based Analytic Methods

Described herein is a method of exposing cells from a population to at least two different reagents, wherein each cell is exposed to the reagents individually, or in groups of two of more. The method entails distributing cells from the population to a plurality of capture sites in a microfluidic device so that a plurality of capture sites each has one or more captured or isolated cells. In various embodiments, the capture sites have groups of 2, 3, 4, 5, 6, 7, 8, 9, 10, 50, 100, 200, 300, 400, 500, 600, 700, 800, 900, or 1000 cell(s) or groups having a number of cells within a range defined by any of these values. In some embodiments, these values are defined by taking an average of the number of cells per capture site.

One or more first reagent(s) is provided to each capture site, and one or more second reagent(s) is provided to each capture site, wherein the second reagent(s) is/are different from the first reagent(s) and is/are provided separately from the first reagent(s). Each pair of reagents can, for example, be provided to a pair of fluidically isolatable chambers in the capture site that are distinct from one another and, optionally, distinct from a chamber including the capture feature.

In some embodiments, at least one surface of the microfluidic device is transparent to permit visualization of the cell or a signal from a label. In such embodiments, the method can optionally include imaging the cell-occupied capture sites before conducting the reaction.

One or more of the reagents can be an agent that supports cellular growth, modulates cellular behavior, and/or facilitates detection of a cellular component (whether on the surface of the cell or intracellular). Indeed, the reagent can be any molecule or composition that one might wish to contact with a cell or its contents. Examples of analyses that can be carried out on single cells or groups of cells in a population can be found in U.S. Patent Publication No. 20130323732, which is incorporated herein by reference in its entirety and for this description. Reagents useful in these analyses are described in U.S. Patent Publication No. 20130323732 and/or will be known to those of skill in the art.

In some embodiments, a reaction is carried out at each capture site (separately from every other capture site), whereby the reaction products encode an item of capture site information. The reaction products can be recovered from the microfluidic device and subjected to further analysis. This further analysis can include the identification of particular reaction products as having been derived from a single cell or group of cells at a particular capture site, e.g., based, at least in part, on the item of capture site information.

In some embodiments, the method entails incorporating nucleic acid sequences into reaction products from a cell population, wherein the nucleic acid sequences are incorporated into the reaction products of each cell individually or of groups of cells. In various embodiments, the nucleic acid sequences are individually incorporated into separate groups of 2, 3, 4, 5, 6, 7, 8, 9, 10, 50, 100, 200, 300, 400, 500, 600, 700, 800, 900, or 1000 cell(s) or into groups having a number of cells within a range defined by any of these values. In some embodiments, these values are defined by taking an average of the number of cells per capture site. The method entails distributing cells from the population to a plurality of capture sites in a microfluidic device so that a plurality of capture sites each comprises not more than a single cell or, where cells are to be analyzed in groups, not more than the desired number of cells for each group of cells. In some embodiments, the capture sites are capable of being fluidically isolated from one another, for example, after cell distribution throughout the device. In certain embodiments, the capture sites each have a capture feature that retains the cell or group of cells in the place. In some embodiments, the capture feature resides within a chamber that can be fluidically isolated from other chambers within the capture site.

In some embodiments, a reaction is conducted in which nucleic acid sequences are incorporated into the reaction products of each cell or group of cells, individually. As those of skill in the art readily appreciate, if the reaction is directed at intracellular templates or targets, such as mRNA or genomic DNA, the method will typically entail a cell permeabilization or lysis step to expose one or both reagents to the intracellular template/target.

The reaction products are then recovered and analyzed in a way that permits the identification of particular reaction products as having been derived from a single cell or group of cells at a particular capture site. One way that this identification can be achieved is by incorporating a barcode into the reaction products. Such a barcode can encode an item of capture site information. Barcodes can be of virtually any length, although where the reaction products are to be subjected to DNA sequencing, shorter barcodes (e.g., 4-6 nucleotides in length) may be preferred in some embodiments. In various embodiments, suitable barcodes are 2, 3, 4, 5, 6, 7, 8, 9, 10, 11, 12, 13, 15, 16, 17, 18, 19, or 20 nucleotides in length or can fall within a range bounded by any of these values, e.g., 2-10 or 3-8.

Figure 11:
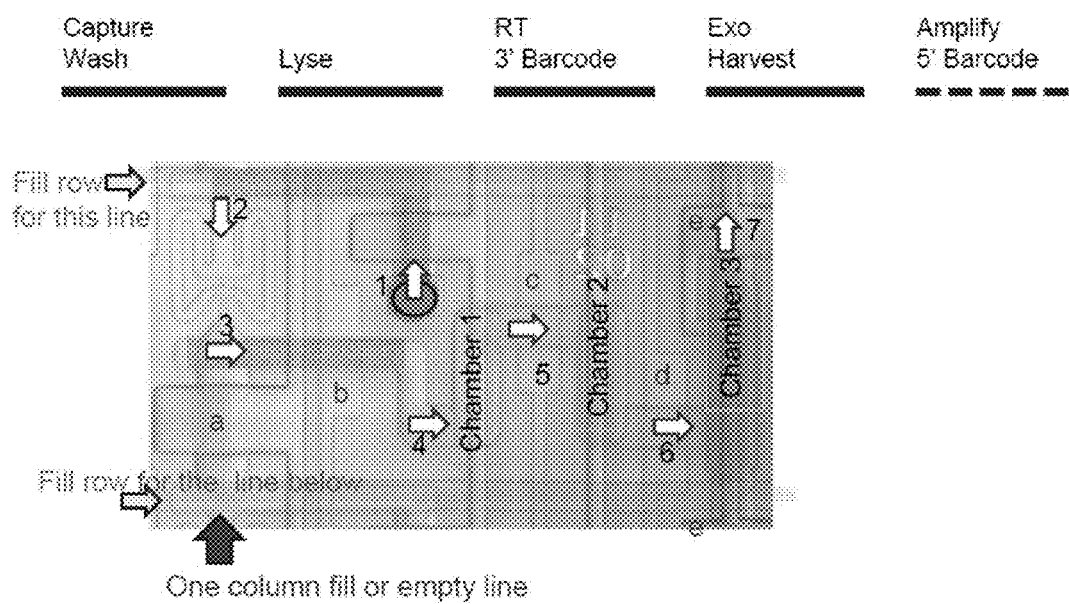
FIG. 11: An illustrative capture site suitable for practicing the single-cell transcriptome identification scheme of FIG. 10. Workflow is shown above a photomicrograph labeled to show four chambers, separated by 4 valves (a-e), as well as fluid flow through the capture site (1-7).
Figure 12:
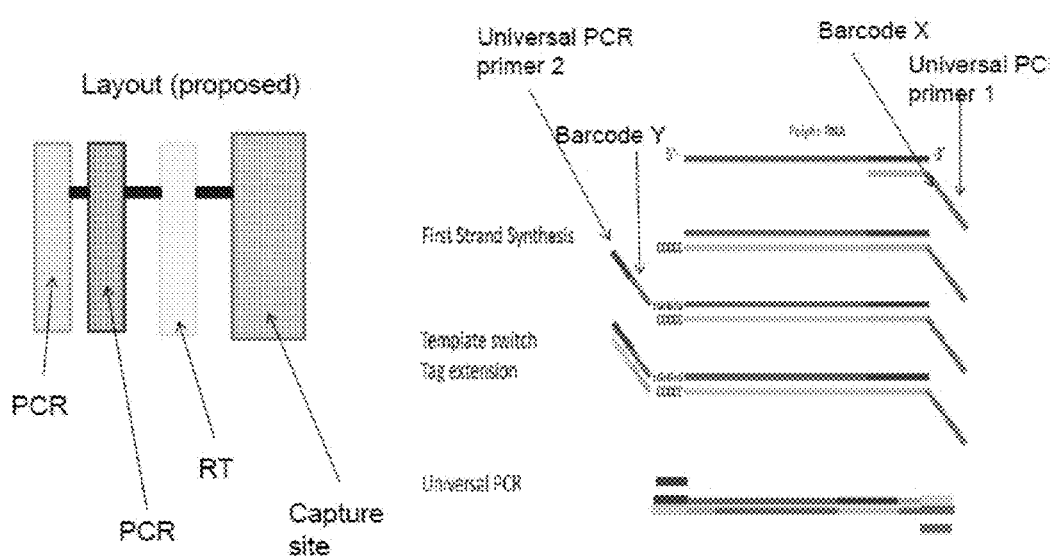
FIG. 12 shows the same scheme for single-cell transcriptome identification as FIG. 10 to the right of a proposed layout for four chambers of a capture site.
Figure 13:
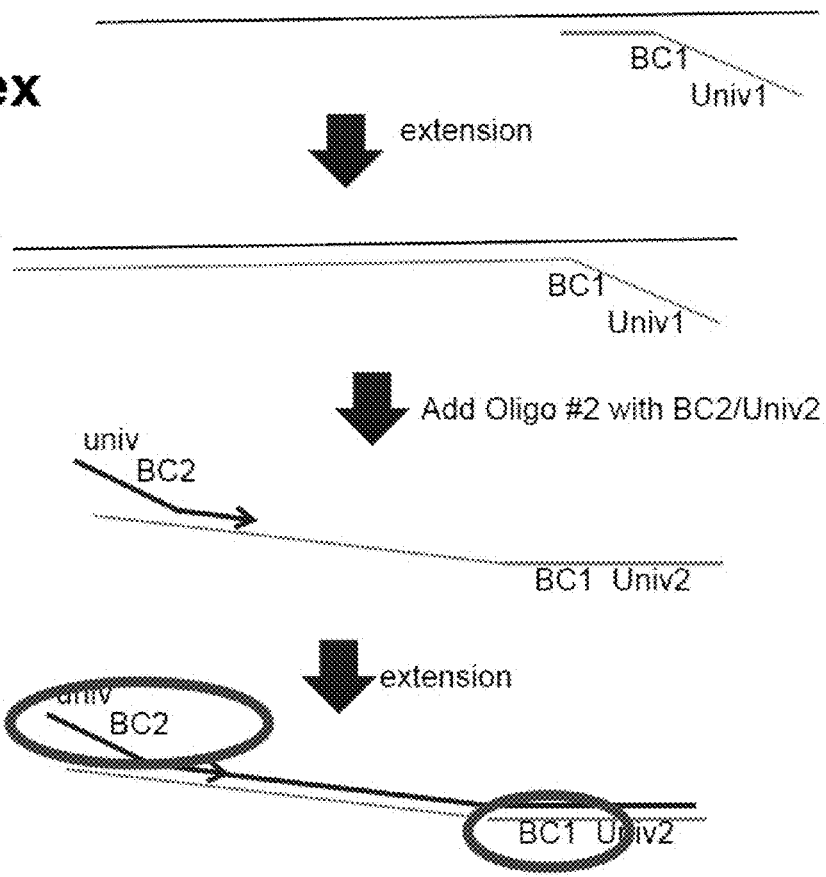
FIG. 13: An illustrative scheme for combinatorial barcoding of nucleic acid (BC1+2=two different barcodes; Univ1 and Univ2=universal primer binding sites, which can be the same or different).
Figure 14:
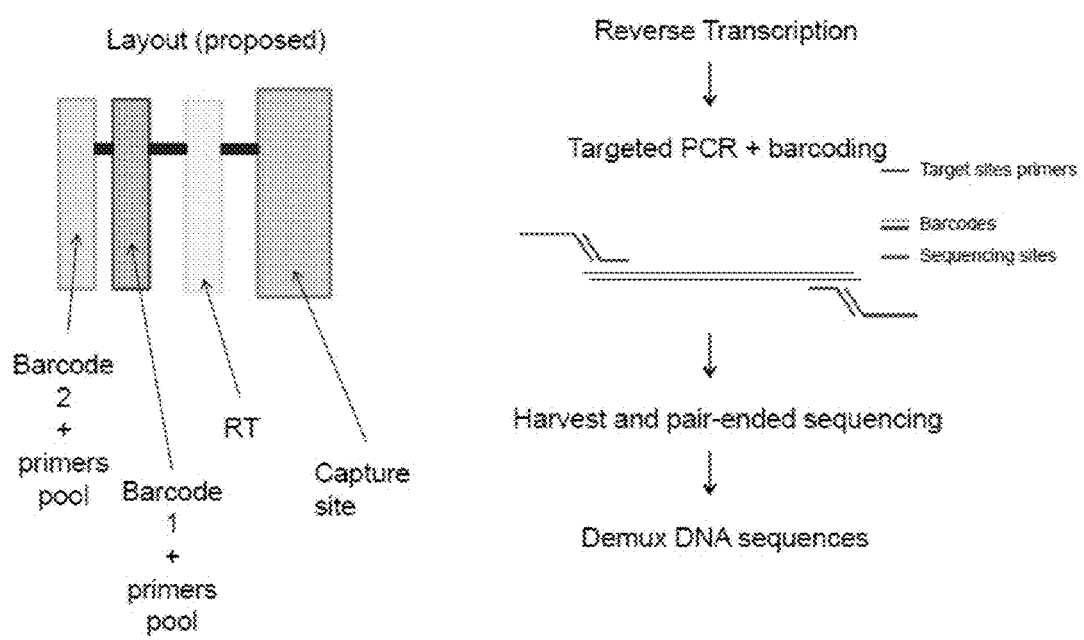
FIG. 14: An illustrative scheme for target-specific amplification of RNA, with combinatorial barcoding, followed by paired-end sequencing.

This method finds particular application in the analysis of nucleic acids, either DNA or RNA from cells, although other molecules (proteins, carbohydrates, lipids, etc.) can be analyzed, and the method can be applied to the analysis of any particle or group of particles (e.g., cellular organelles, liposomes, etc.) Virtually any type of reaction or series of reactions can be performed in the method. In certain embodiments, the reaction introduces nucleic acid sequences into the nucleic acids of a cell or group of cells. In these embodiments, the reaction may include reverse transcription, amplification, ligation or any other reaction that can be performed on a nucleic acid. Examples include whole transcriptome amplification (WTA; see illustrative embodiments shown in FIGS. 10-12), whole genome amplification (WGA; see illustrative embodiment shown in FIG. 13), microRNA (mRNA) preamplification, target-specific amplification of RNA (see illustrative embodiment shown in FIG. 14) or DNA (see illustrative embodiment shown in FIG. 13, wherein the template-specific portion of each primer is target-specific), protein proximity ligation (see illustrative embodiment shown in FIG. 16), and transposition (see illustrative embodiment shown in FIG. 17).

The methods described herein can be used to analyze nucleic acids from any type of cells, e.g., any self-replicating, membrane-bounded biological entity or any non-replicating, membrane-bounded descendant thereof. Non-replicating descendants may be senescent cells, terminally differentiated cells, cell chimeras, serum-starved cells, infected cells, non-replicating mutants, anucleate cells, intact nuclei, and fixed, intact (dead) cells, etc. Cells used in the methods described herein may have any origin, genetic background, state of health, state of fixation, membrane permeability, pretreatment, and/or population purity, among other characteristics. Suitable cells may be eukaryotic, prokaryotic, archaeon, etc., and may be from animals, plants, fungi, protists, bacteria, and/or the like. In illustrative embodiments, human cells are analyzed. Cells may be from any stage of organismal development, e.g., in the case of mammalian cells (e.g., human cells), embryonic, fetal, or adult cells may be analyzed. In certain embodiments, the cells are stem cells. Cells may be wildtype; natural, chemical, or viral mutants; engineered mutants (such as transgenics); and/or the like. In addition, cells may be growing, quiescent, senescent, transformed, and/or immortalized, among other states. Furthermore, cells may be a monoculture, generally derived as a clonal population from a single cell or a small set of very similar cells; may be presorted by any suitable mechanism, such as affinity binding, FACS, drug selection, etc.; and/or may be a mixed or heterogeneous population of distinct cell types.

One advantage of the methods described herein is that they can be used to analyze virtually any number of single cells. In various embodiments, the number of single cells analyzed can be about 10, about 50, about 100, about 500, about 1000, about 2000, about 3000, about 4000, about 5000, about 6000, about 7,000, about 8000, about 9,000, about 10,000, about 15,000, about 20,000, about 25,000, about 30,000, about 35,000, about 40,000, about 45,000, about 50,000, about 75,000, or about 100,000 or more. In specific embodiments, the number of cells analyzed can fall within a range bounded by any two values listed above.

Figure 18:
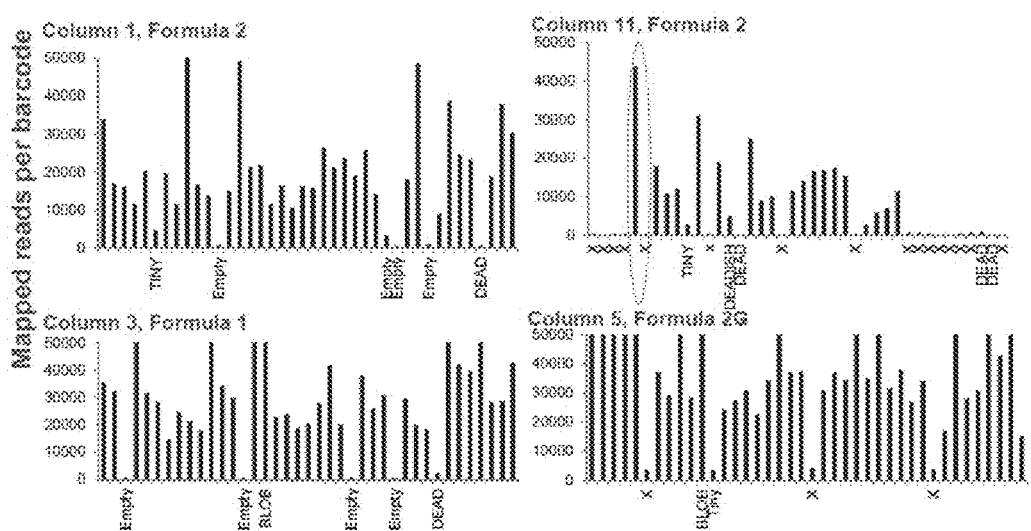
FIG. 18: Illustrative data from a sequencing study in which sequences were barcoded on a matrix-type microfluidic device, followed by sequencing, and "demultiplexing" using column and row barcode to attribute particular sequencing reads to particular capture sites.
Figure 19:
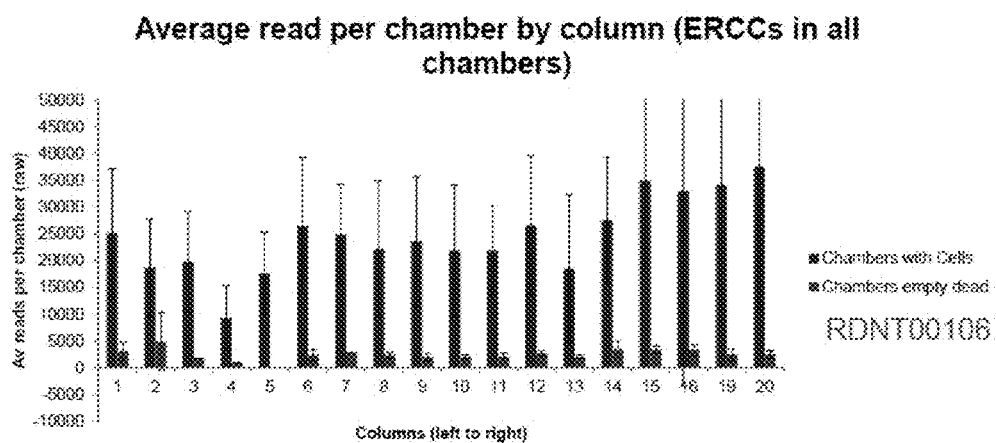
FIG. 19: Illustrative data from a sequencing study in which sequences were barcoded on a matrix-type microfluidic device, followed by sequencing, and "demultiplexing" using column and row barcode to attribute particular sequencing reads to particular capture sites.

In some embodiments, this method can be carried out on a matrix-type microfluidic device (described further below), which facilitates the introduction of a barcode that identifies a particular row in the device and a barcode that identifies a particular column, whereby the combination uniquely identifies a particular capture site and therefore a particular cell or group of cells from which the reaction products were derived. The method has been tested on such a device and demonstrated to work (see results shown in FIGS. 18 and 19).

In some embodiments, each reaction can incorporate at least one UMI, which is a nucleic acid sequence that uniquely identifies the molecule into which it is incorporated. In variations of such embodiments, the reaction incorporates one or more barcodes in addition to one or more UMIs. UMIs can be any length, and the length required for a given analysis will increase as the number of unique molecules to be identified increases. In various embodiments, suitable UMIs are 2, 3, 4, 5, 6, 7, 8, 9, 10, 11, 12, 13, 15, 16, 17, 18, 19, or 20 nucleotides in length or can fall within a range bounded by any of these values, e.g., 2-10, 3-8, 4-7, or 5-6.

The combined use of beads and/or sequence tags to label RNA or DNA for analysis may avoid a need for preamplification prior to analysis and makes the matrix-type microfluidic device reusable.

RNA Analysis

In some embodiments, the above-described methods are applied to RNA analysis. In this case, the reaction(s) carried out at each capture site can include reverse transcription of RNA, e.g., second-strand synthesis to produce cDNA.

Figure 10:
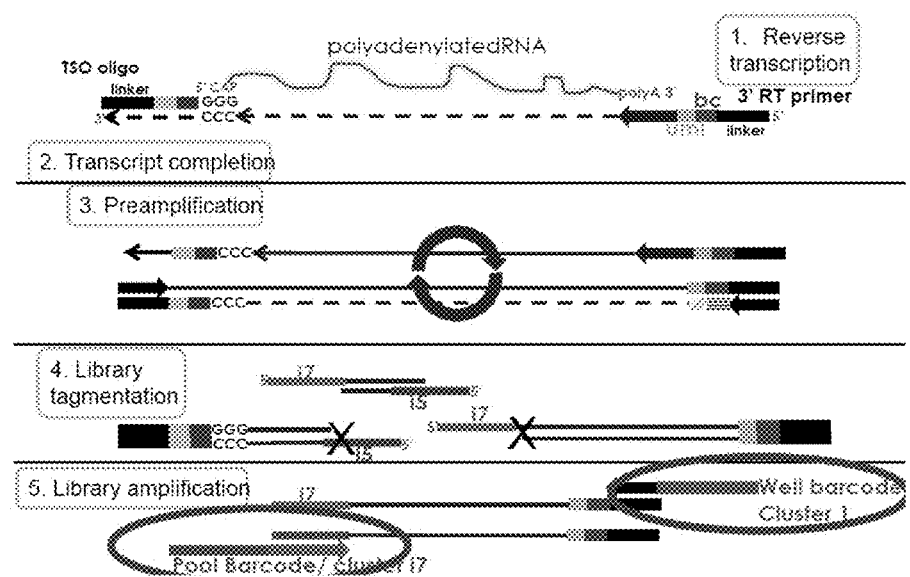
FIG. 10: A scheme for single-cell transcriptome identification (for messenger [poly-A] RNA) and 3' end counting of the transcripts, which is described in Example 2.

In particular methods suitable, for example, for transcriptome analysis (e.g., in single cells or in groups of cells as described above) the first reagent(s) can include a reverse transcription (RT) primer. An illustrative RT primer is shown in FIG. 10 ("3' RT primer"). This RT primer includes a first barcode ("bc") 5' of a poly-dT sequence. The poly-dT sequence should be sufficiently long to anneal to the poly-A tails of mRNA, typically on the order of 18-30 nucleotides in length. This RT primer optionally includes a first UMI, which is also preferably 5' of the poly-dT sequence. FIG. 10 shows the first barcode 5' of the UMI; however, those of skill in the art appreciate that the order of these elements may be reversed. As shown in FIG. 10, the RT primer can additionally include a first linker, preferably at the 5' end of the RT primer. The first linker can be used to facilitate unbiased amplification and, wherein DNA sequencing is to be carried out, 3' end enrichment after tagmentation. In some embodiments, the RT primer additionally comprises an anchor sequence 3' of the poly-dT sequence. The length and composition of the anchor sequence can vary, and the selection of a suitable anchor sequence for a particular analysis is within the level of skill in the art. Typically, the anchor sequence is at least two nucleotides in length.

In some embodiments, the second reagent(s) comprise a 5' oligonucleotide comprising a poly-riboG sequence. An illustrative oligonucleotide of this type is shown in FIG. 10. This oligonucleotide is identified as "TSO oligo" for "template-switching oligonucleotide." This 5' oligonucleotide can include a second barcode 5' of the poly-riboG sequence (shown, e.g., in FIG. 10 as one of the two bars between the poly-riboG sequence and a linker). The 5' oligonucleotide can optionally include a second UMI, which can be the same as or different from the first UMI, which is also preferably 5' of the poly-riboG sequence (shown, e.g., in FIG. 10 as the other to the two bars between the poly-riboG sequence and the linker). As shown in FIG. 10, the 5' oligonucleotide can additionally include a second linker, preferably at the 5' end of the 5' oligonucleotide. The second linker can be the same as or different from the first linker, and like the first linker, can be used to facilitate unbiased amplification.

In particular embodiments, the method is carried out in a microfluidic device, as described below. In this case, the RT primer can be delivered to capture sites via one set of the input lines, and the 5' oligonucleotide can be delivered to the capture sites via the other set of input lines.

In certain embodiments, the use of these two reagents in one of the above-described methods produces cDNA wherein one strand has the structure: 5'-second linker-nucleotide sequence derived from RNA-first linker-3', with at least one barcode located in between the linkers. In a variation of this embodiment, the first barcode is located adjacent to the first linker and/or the second barcode is located adjacent to the second linker. For example, one strand of the cDNA can have the structure:

3'-second linker-poly dC-nucleotide sequence derived from RNA-first barcode-first linker-5'.

Where a second barcode is included, one strand of the cDNA can have the structure:

3'-second linker-second barcode-poly dC-nucleotide sequence derived from RNA-first barcode-first linker-5'.

The inclusion of a UMI can produce, for example:

3'-second linker-poly dC-nucleotide sequence derived from RNA-first UMI-first barcode-first linker-5'; or 3'-second linker-poly dC-nucleotide sequence derived from RNA-first barcode-first UMI-first linker-5'.

And the inclusion of second UMI can produce, for example:

3'-second linker-second barcode-second UMI-poly dC-nucleotide sequence derived from RNA-first UMI-first barcode-first linker-5';

3'-second linker-second barcode-second UMI-poly dC-nucleotide sequence derived from RNA-first barcode-first UMI-first linker-5';

3'-second linker-second UMI-second barcode-poly dC-nucleotide sequence derived from RNA-first UMI-first barcode-first linker-5'; or 3'-second linker-second UMI-second barcode-poly dC-nucleotide sequence derived from RNA-first barcode-first UMI-first linker-5'.

DNA Analysis

As those of skill in the art appreciate, the chemistry described above for RNA analysis can be adapted to DNA analysis, e.g., where the reaction(s) carried out at each capture site includes amplification of DNA.

In particular DNA amplification embodiments, the first and/or second reagent(s) include first and/or second amplification primers, respectively, wherein the first and/or second amplification primers comprise a first or second barcode, respectively, that is 5' of a primer sequence. The primer sequence(s) can be random or designed to amplify a particular target nucleic acid (i.e., "target-specific"). In some embodiments, the first and/or second amplification primers may additionally include a first or second UMI, respectively. Any UMI is preferably 5' of the primer sequence. In some embodiments, the first and/or second amplification primer additionally includes a first or second linker, preferably at the 5' end(s) of the primer(s), e.g., to facilitate unbiased amplification. The discussion above regarding suitable lengths and sequences for barcodes and UMIs apply equally in the DNA analysis context. For primers including barcodes and UMIs, their positions relative to one another are not critical.

In particular embodiments, DNA amplification is carried out in a microfluidic device, as described below. In this case, the first amplification primer can be delivered to capture sites via one set of the input lines, and the second amplification primer can be delivered to the capture sites via the other set of input lines.

In certain embodiments, the use of two such amplification primers in one of the above-described methods produces an amplicon, wherein one strand has the structure: 5'-second linker-nucleotide sequence derived from sample DNA-first linker-3', with a barcode located in between the linkers. For example, one strand of the amplicon can have the structure:

3'-second linker-nucleotide sequence derived from sample DNA-first barcode-first linker-5'.

Where a second barcode is included, one strand of the amplicon can have the structure:

3'-second linker-second barcode-nucleotide sequence derived from sample DNA-first barcode-first linker-5'.

The inclusion of a UMI can produce, for example:

3'-second linker-nucleotide sequence derived from sample DNA-first UMI-first barcode-first linker-5'; or
3'-second linker-nucleotide sequence derived from sample DNA-first barcode-first UMI-first linker-5'.

And the inclusion of second UMI can produce, for example:

3'-second linker-second barcode-second UMI-nucleotide sequence derived from sample DNA-first UMI-first barcode-first linker-5';
3'-second linker-second barcode-second UMI-nucleotide sequence derived from sample DNA-first barcode-first UMI-first linker-5';
3'-second linker-second UMI-second barcode-nucleotide sequence derived from sample DNA-first UMI-first barcode-first linker-5'; or
3'-second linker-second UMI-second barcode-poly dC-nucleotide sequence derived from sample DNA-first barcode-first UMI-first linker-5'.

In any of the above-described methods, all of the method steps can, but need not, be performed in a microfluidic device.

Any of these methods can optionally include preamplification, most conveniently, after addition of linkers to either end of the cDNA or DNA. For example, preamplification can be carried out to increase the levels of the cDNA or amplicons before further characterization (such as, e.g., DNA sequencing). Preamplication can be carried out using linker primers that anneal to the first and second linkers, wherein the linker primers are the same or different (depending on whether the linkers themselves are the same or different). Preamplification can be carried out in the microfluidic device or after exporting reaction products from the device.

In some embodiments, any of the above methods can be carried out to prepare templates for DNA sequencing. In such embodiments, the reaction performed in the microfluidic device can incorporate one or more DNA sequencing primer binding sites into the reaction products, or these sites can be incorporated into the reaction products after export from the microfluidic device. In specific embodiments, DNA sequencing primer binding sites can be added by tagmentation, which is a well-known transposase-based in vitro shotgun method in which the DNA to be sequenced is simultaneously fragmented and tagged with transposon ends to introduce sequences that facilitate subsequent sequencing.

Accordingly, in some embodiments, the methods include subjecting the reaction products to DNA sequencing, e.g., Sanger sequencing, next-generation sequencing (e.g., bridge sequencing), or third-generation sequencing. In variations of such embodiments, the sequences obtained from DNA sequencing can be identified as having been derived from a particular capture site based on one or two barcodes.

As discussed in more detail below, reaction products from a particular row or column of a matrix-type microfluidic device can be exported as a pool. Any subsequent characterization of reaction products, such as DNA sequencing, can be carried out on individual exported pools. However, it is also contemplated that the pools themselves can be pooled prior to further characterization. In this case, the reaction product(s) from each separate capture site in the microfluidic device is typically distinct, which is readily achieved, e.g., by using two barcode sequences to encode the row and column location of the capture site in the microfluidic device.

Primer Combinations

Any of the primers or oligonucleotides described above may be combined to form primer combinations. Typically, primer combinations include 2, 3, 4, or more primers or oligonucleotides that are used together in a method such as those described herein.

For example, a primer combination for use in producing cDNA from RNA (first strand synthesis) can include:

(a) a reverse transcription (RT) primer including an anchor sequence, a poly-dT sequence 5' of the anchor sequence, a first barcode 5' of the poly-dT sequence, and a first linker 5' of the first barcode sequence; and (b) a 5' oligonucleotide including a poly-riboG sequence, a second barcode 5' of the poly-riboG sequence, and a second linker 5' of the second barcode.

In certain embodiments, one or both of these primers can include a UMI.

An illustrative primer combination for use in amplifying DNA can include first and second amplification primers that each include: a primer sequence; a barcode that is 5' of the primer sequence, wherein the barcodes in each primer are different; and a linker that is 5' of the barcode; wherein one or both primers also include a UMI that is 5' of the primer sequence and 3' of the linker.

These primer combinations can also include one or more linker primer(s) that anneal(s) to the linkers, e.g., to facilitate unbiased amplification. In some embodiments, the combination includes two linker primers: a 5' linker primer and a different 3' linker primer. In some embodiments requiring preamplification of cDNA or amplicons produced using the above primer combinations, one or both linker primers can be used to carry out this preamplification.

A primer combination intended for use in preparing DNA sequencing templates for bridge sequencing can optionally include a primer including a portion specific for the 3' linker primer or its complement and/or a primer including a portion specific for the 5' linker primer or its complement, wherein the primer(s) additionally include a flow cell sequence useful in cluster generation in bridge sequencing. The flow cell sequence is generally 5' of the linker-specific portion.

Matrix-Type Microfluidic Devices

In certain embodiments, a matrix-type microfluidic device useful in the method described above includes capture sites arranged in a matrix of R rows and C columns, wherein R and C are integers greater than 1. Each capture site can include a capture feature that is capable of capturing just one cell or, where cells are to be analyzed in groups, not more than the desired number of cells for each group of cells. The capture sites can be fluidically isolated from one another after distribution of cells to the capture sites. The device also includes a set of R first input lines configured to deliver the first reagent(s) to capture sites in a particular row, and a set of C second input lines configured to deliver second reagent(s) to capture sites in a particular column, wherein this delivery is separate from the delivery first reagent(s). An illustrative device of this type is shown schematically in FIG. 1A. FIG. 1B illustrates the delivery of R different barcodes through the R different first input lines to the capture sites. FIG. 1C illustrates the delivery of C different barcodes through C different input lines to the capture sites. In particular embodiments, all barcodes will be unique, i.e., different from every other barcode provided to the device. FIG. 1D illustrates that, after the reaction has been carried out, reaction products can be harvested from each column as a pool, for example, by applying a harvesting fluid to the C second input lines to push the reaction products out of outlets at one end of the input lines. (Those of skill in the art readily appreciate that reaction products could alternatively be harvested by row in the same manner in a different implementation.) FIG. 2 shows a photograph of the device shown schematically in FIG. 1.

In certain embodiments, the matrix-type microfluidic device permits analysis of individual cells or groups of cells, e.g., up to (and including) 1000. The cells can be intact or partially or fully disrupted (e.g., permeablized or lysed) after capture or isolation of one or more cells at each capture site. In the latter case, the device is configured to provide this functionality (see, e.g., FIG. 11). In some embodiments, the device is transparent on at least one surface to permit imaging to visualize cell number or phenotype (where the cells or their contents have been reacted with an optically detectable label). In some embodiments, the device is configured to perform "X-Y" combinatorial barcoding, whereby reaction products may be exported in one or more pools (which may themselves be pooled) and further analyzed in multiplex (e.g., by amplification), followed by "de-multiplexing" ("demux") to assign particular reaction products to particular capture sites. This type of barcoding is illustrated in FIG. 1, which shows the same set of 3' barcodes ("3'BC" in FIG. 1B) being delivered to each column and the same set of 5' barcodes ("5'BC" in FIG. 1C) being delivered to each row.

Figure 3:
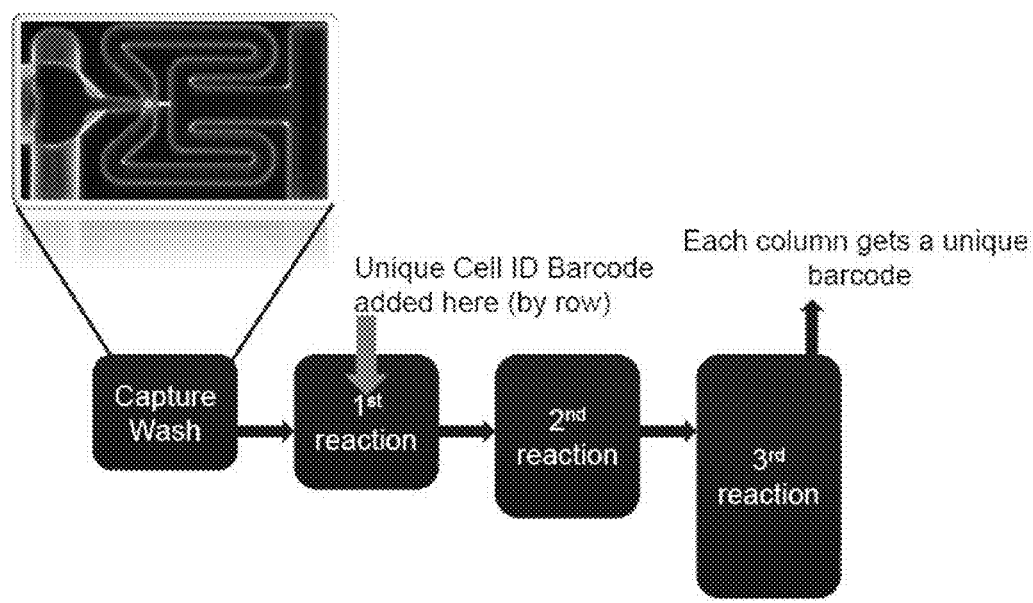
FIG. 3: A photomicrograph of an illustrative capture feature suitable for capturing a single cell in a matrix-type microfluidic device, as well as an illustrative flowchart for a method in which barcodes are added by row and column into the reaction products from the captured cell.
Figure 4E:
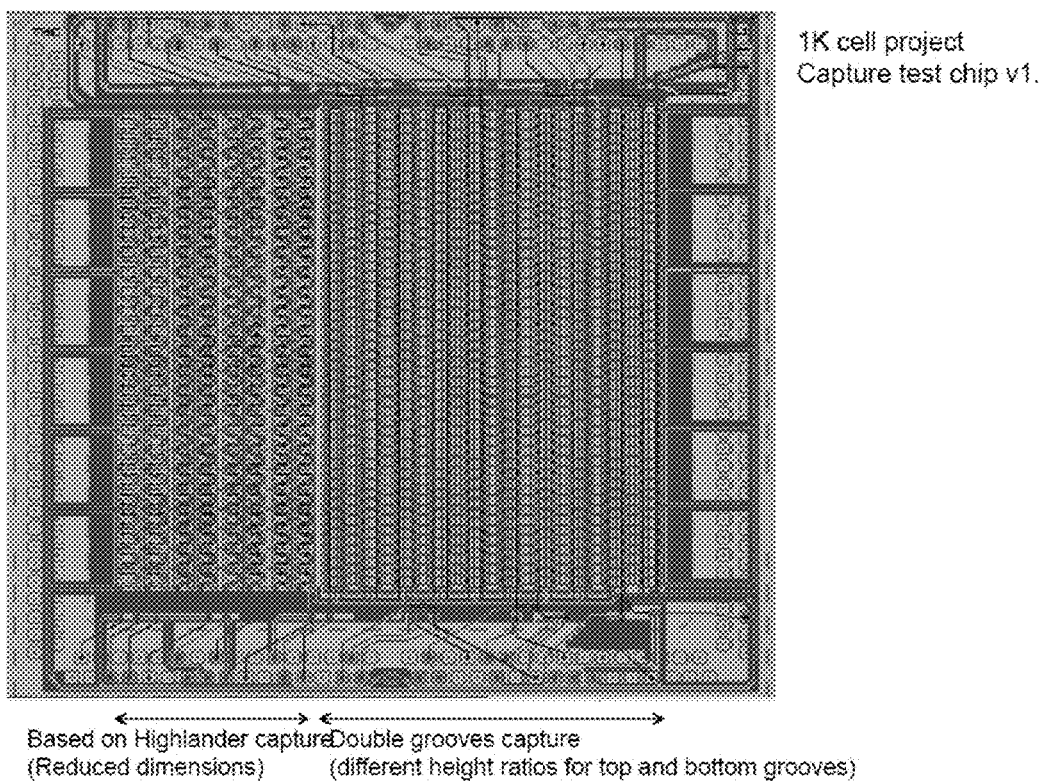

FIG. 3 shows a photomicrograph of an illustrative capture feature suitable for capturing a single cell in such a device, as well as an illustrative flowchart for a method in which barcodes are added by row and column into the reaction products from the captured cell. FIG. 4A shows a series of increasingly more miniaturized capture features, which facilitate the analysis of more cells per chip. FIG. 4B shows the arrangement of capture features in rows and columns, together with the channels for distributing cells to the capture features. FIG. 4C shows photomicrographs of the miniaturized capture features.

Figure 5:
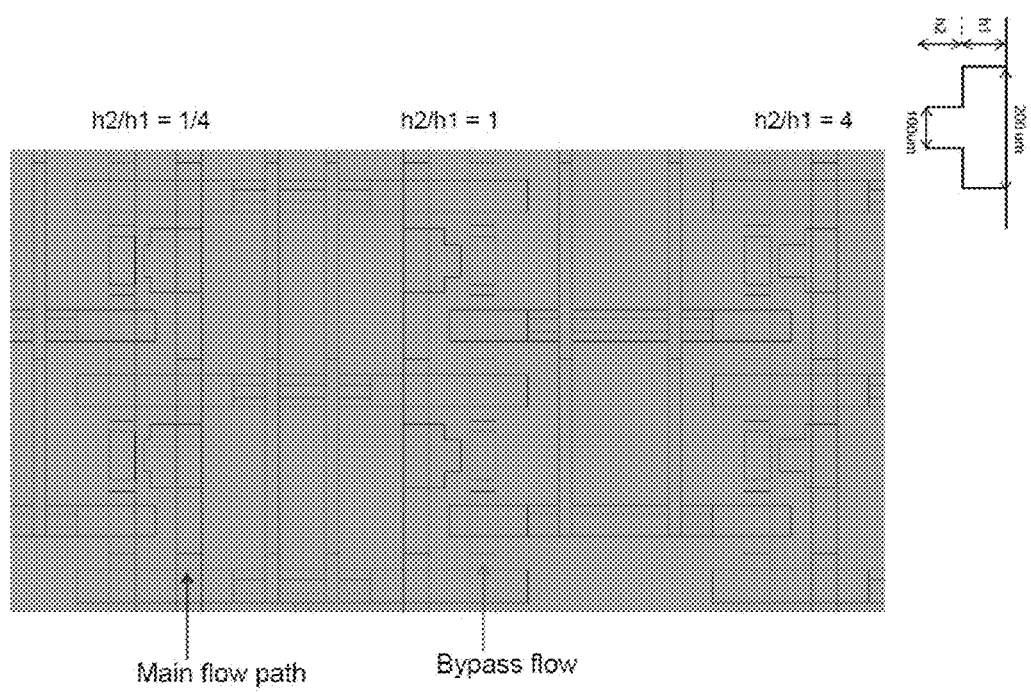
FIG. 5: A schematic of illustrative double grooves capture features including the channels for distributing cells to the capture features. This geometry allows for more capture sites per unit area.
Figure 6:
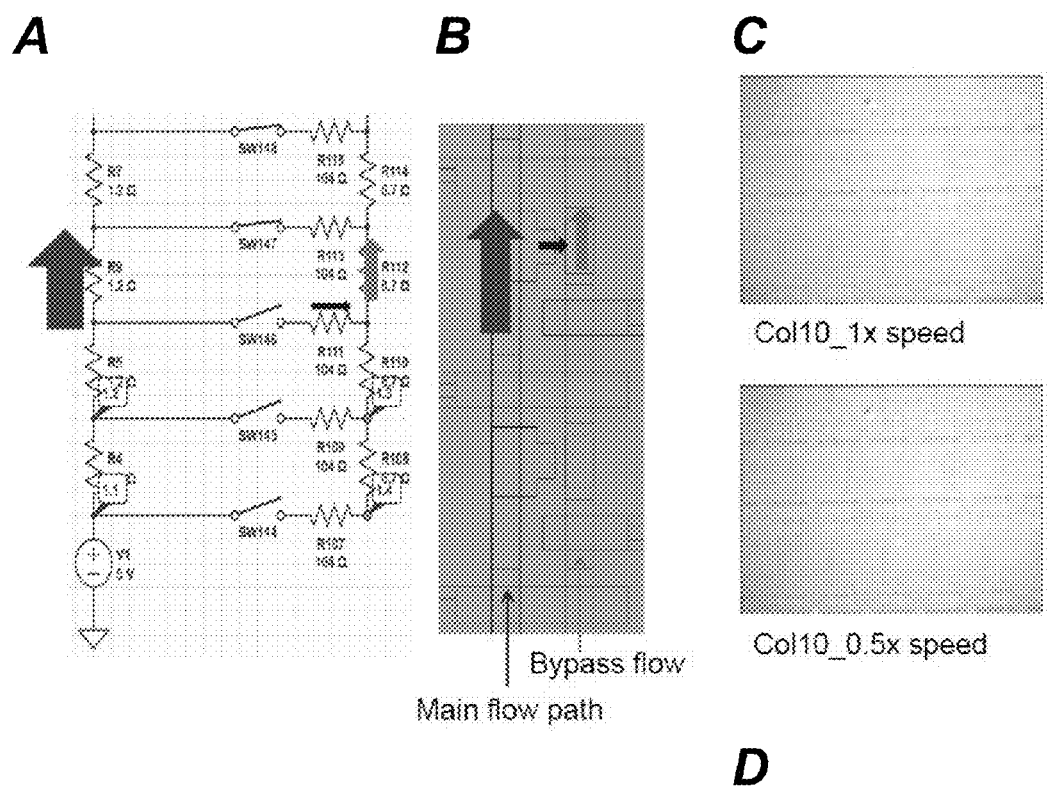
FIG. 6A-D: (A) shows the flow resistance for the main and bypass flow in an illustrative double grooves capture device, illustrated schematically in (B) and in photomicrographs in (C) and (D).
Figure 7:
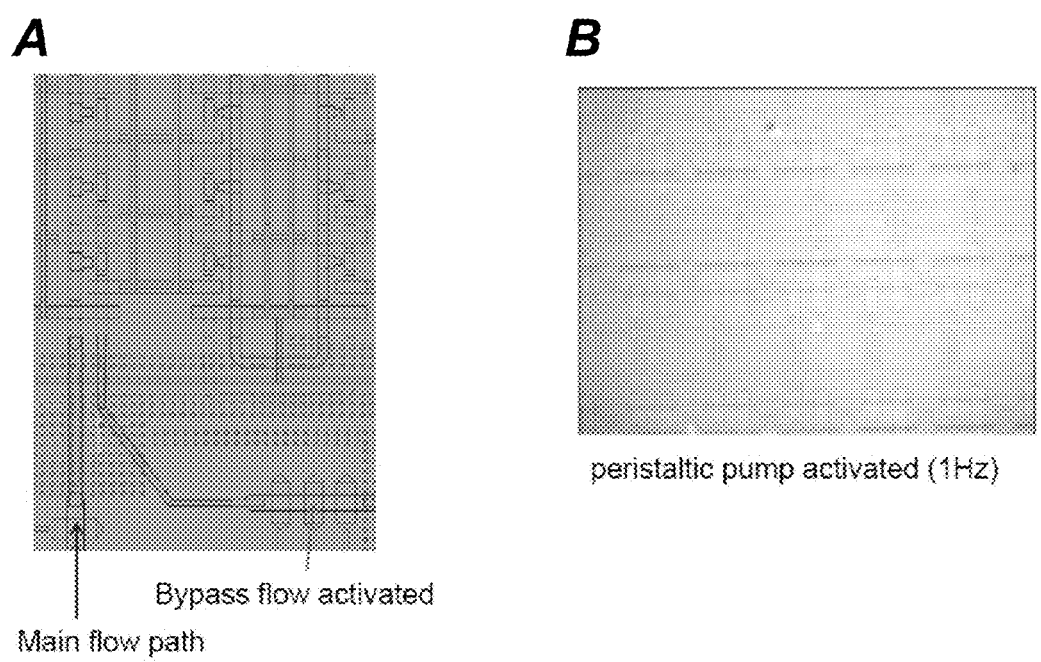
FIG. 7A-B shows the activation of bypass peristaltic pumping in an illustrative double grooves capture device, schematically in (A) and in a photomicrograph in (B).
Figure 8:
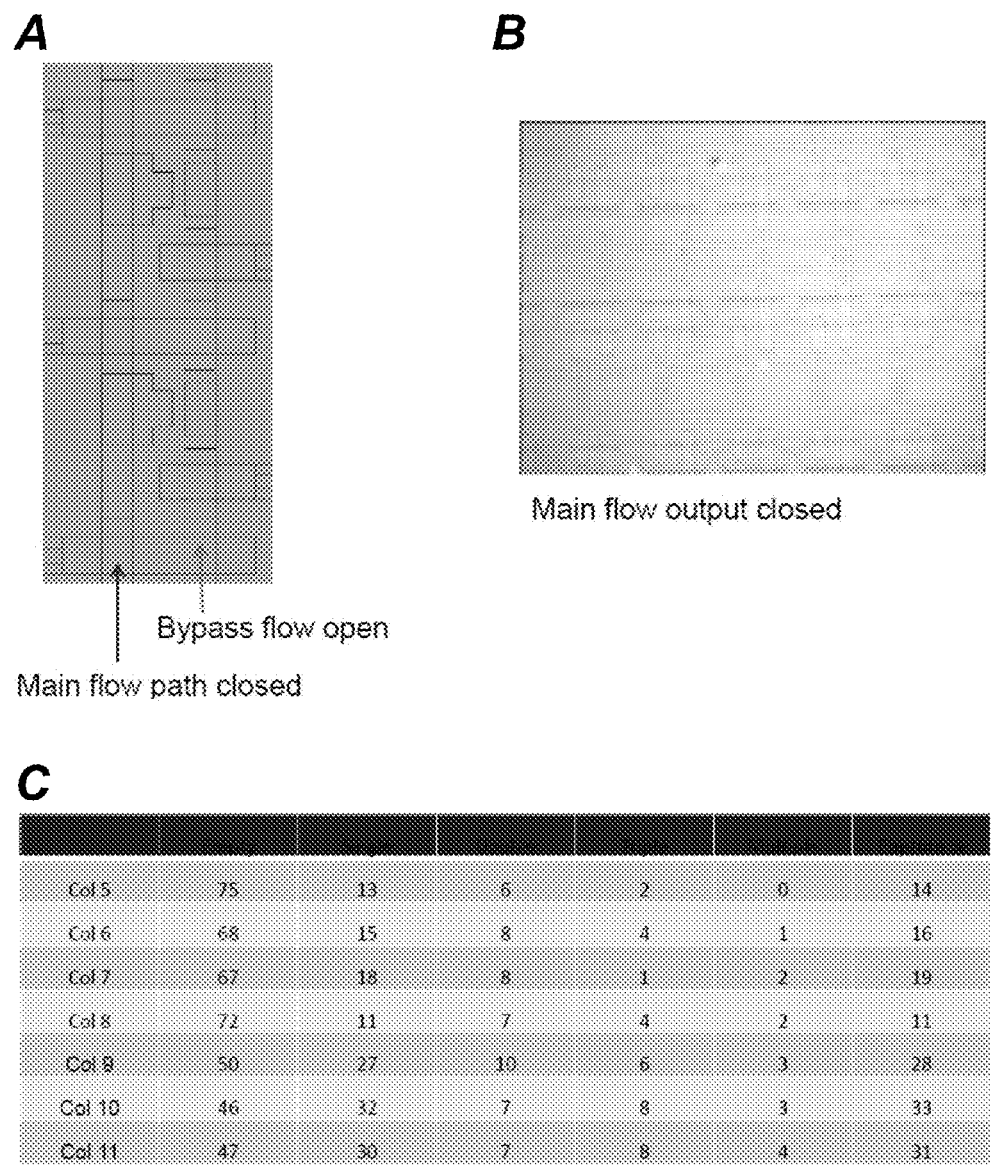
FIG. 8A-C: (A) and (B) illustrate closing the main flow output in an illustrative double grooves capture device, schematically in (A) and in a photomicrograph (B). (C) reports cell occupancy data for the double grooves capture feature design, with number of capture features having no cells in column 1 of the table, and the number of capture features having just 1 cell in column 2 of the table.

The table in FIG. 4D reports the cell occupancy data for two different capture site designs, with the top panel showing the results for the miniaturized features, and the bottom panel showing the results for double grooves capture features with different height ratios for top and bottom grooves. The first column in the table in FIG. 4D reports the number of capture features having no cells, and second column reports the number of capture features having just 1 cell. FIG. 5 shows a schematic of the double grooves capture features including the channels for distributing cells to the capture features. This geometry allows for more capture sites per unit area. FIG. 6A shows the flow resistance for the main and bypass flow in such a device, illustrated schematically in FIG. 6B and in photomicrographs in FIGS. 6C and D. FIG. 7 illustrates the activation of bypass peristaltic pumping in such a device, schematically in panel A and in a photomicrograph in panel B. FIGS. 8A and B illustrates closing the main flow output in such a device, schematically in panel A and in a photomicrograph in panel B. The table in FIG. 8C reports cell occupancy data for the double grooves capture feature design, with number of capture features having no cells in column 1 of the table, and the number of capture features having just 1 cell in column 2 of the table.

Figure 9:
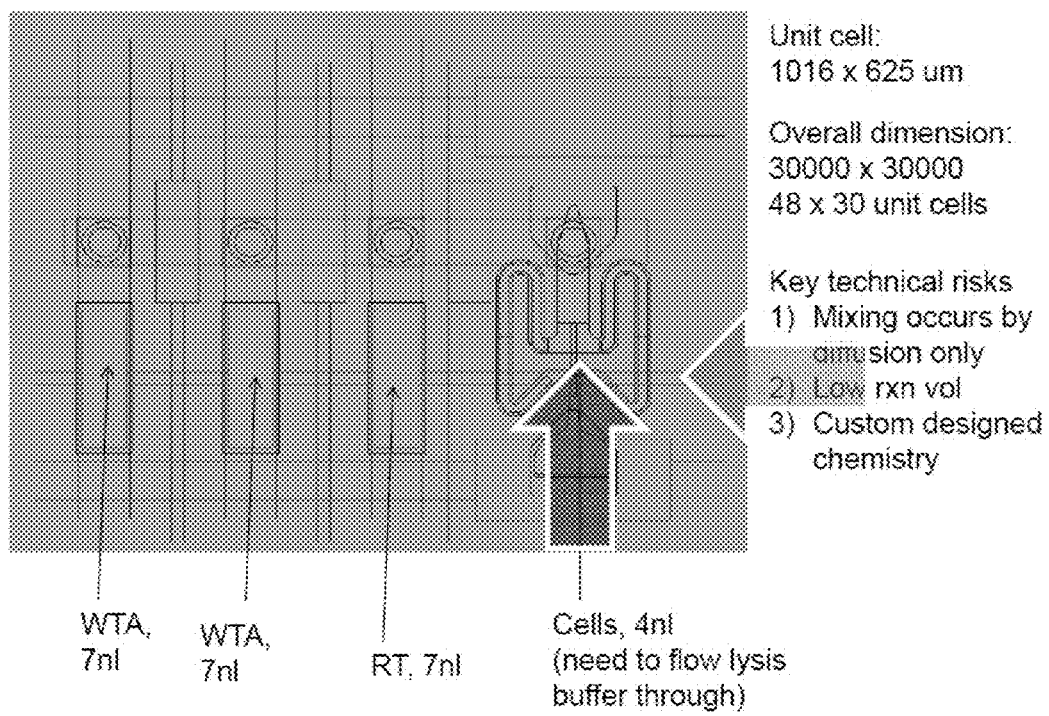
FIG. 9: An illustrative unit capture site with four chambers, each of which is available for reagent(s). The capture feature is located in one of these four chambers. In use, a first reagent(s) can be loaded into the capture site from bottom to top (purple arrow), and a second reagent can be loaded into a capture site from left to right (green arrow).

FIG. 9 shows an illustrative unit capture site with four chambers, each of which is available for reagent(s). The capture feature is located in one of these four chambers. In use, a first reagent(s) can be loaded into the capture site from bottom to top (purple arrow), and a second reagent can be loaded into a capture site from left to right (green arrow).

In various embodiments, a microfluidic device having from about 97 to about 1000 separate capture sites is employed to carry out one or more of the methods described herein, particularly from about 97 to about 9000 capture sites, more particularly from about 97 to about 8000 capture sites, and even more particularly from about 97 to about 7500 capture sites. In some embodiments the microfluidic device can have greater than 100, greater than 200, greater than 300, greater than 400, greater than 500, greater than 600, greater than 700, greater than 800, greater than 900, or greater than 1000 capture sites.

In some embodiments, the capture sites have one or more reaction chambers ranging from about 2 nL to about 500 nL. The lower the reaction chamber volume, the higher the effective concentration of any target nucleic acid. In certain embodiments, the reaction chamber is from about 2 nL to about 50 nL, preferably 2 nL to about 25 nL, more preferably from about 4 nL to about 15 nL. In some embodiments, the reaction chamber volume is 5 nL, 6, nL, 7 nL, 8 nL, 9 nL, 10 nL, 11 nL, or 12 nL, or falls within any range bounded by any of these values.

Microfluidic devices meeting the specifications described herein, and systems employing them the carry out the disclosed method can be designed and fabricated based on the guidance herein and in prior co-owned patent publications, such as U.S. Patent Publication No. 2013/0323732, published May 12, 2013, Anderson et al. (hereby incorporated by reference for their descriptions of single-cell analysis methods and systems). For example, the $C_1$™ Single-Cell Auto Prep System available from Fluidigm Corporation (South San Francisco, Calif.) provides bench-top automation of the multiplexed isolation, lysis, and reactions on nucleic acids from single cells in an IFC™. In particular, the $C_1$ Single-Cell Auto Prep Array™ IFC is a matrix-type microfluidic device that facilitates capture and highly paralleled preparation of 96 individual cells. When used properly, each capture site within the chip captures one single cell. Sometimes, a site may capture zero, two, or more cells; however, the exact number of captured cells in each captured site of a $C_1$ chip is easily verified at high confidence and easily documented in a microscopic picture. In certain embodiments, cells are captured and barcoding is carried out in each separate reaction volume to produce barcoded nucleic acid molecules, which are analyzed, most conveniently by DNA sequencing, be it Sanger sequencing, next-generation sequencing, or third-generation sequencing, optionally after preamplification.

Kits

Kits according to the invention can include one or more reagents useful for practicing one or more methods described herein. A kit generally includes a package with one or more containers holding the reagent(s), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay. In specific embodiments, the kit includes one or more matrix-type microfluidic devices and/or primers/oligonucleotides discussed above or combinations thereof.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

High-Throughput (HT) IFC™

Various designs for a high-throughput (HT) IFC™ are shown in the accompanying figures. One aspect of the HT IFC™ is that it contains modified (miniaturized) capture features that enable eight times the number of capture sites in the same area as a normal IFC™.

Another aspect of the HT IFC™ is that it enables the multiplexing of barcodes and this, combined with companion chemistry, such as that described below, allows the HT IFC™ to go beyond the current 96 single-cell limit of C1™ system. Specifically, the HT IFC™ can individually address each chamber with up to two inputs, permitting the separate addition of at least two different barcodes in discrete liquid additions to a single cell.

Example 2

Companion Chemistry for HT IFC™ for Transcriptome Analysis

The chemistry to enable barcoding and cell de-multiplexing on an HT IFC™ can include a set of modified oligonucleotides that allow single-cell transcriptome identification (for messenger [poly-A] RNA) and 3' end counting of the transcripts used with conventional, commercially-available reverse transcriptase enzymes (MuMLV Rnase H activity mutants) and conventional TaqPolymerases, as well as the Nextera XT™ kit. The set can include one or more of the following (see FIG. 10, wherein the numbers correspond to the oligonucleotide numbers give below):

1. An oligonucleotide (RT primer, referred to as a 'row' barcode in the context of the HT IFC™) directed at the 3' end of an mRNA transcript minimally including an 2-nucleotide anchor sequence, a poly-dT sequence (18-30 dTs), a chamber identification barcode of between 4-6 nucleotides, an optional randomer of 5-6 nucleotides for single molecule identification (UMI), and a linker sequence for unbiased amplification and 3' end enrichment after tagmentation.

2. An oligonucleotide that allows completion of the cDNA molecule from the 5' end of the transcript and linker add-on for unbiased amplification. This oligonucleotide includes an optional 4-5-nucleotide barcode as well as an optional 5-nucleotide randomer for single molecule identification (UMI) along with the linker sequence for amplification at the 5' end.

3. An oligonucleotide that facilitates preamplification of the linkers appended to either end of the first strand of cDNA.

4. An oligonucleotide (cluster 2) specific for the 3' end linker that allows for enrichment of the 3' end of the transcript following tagmentation, used during the addition of the flow cell sequence. An optional oligonucleotide directed at the 5' linker to enrich for the 5' end of the transcript may also be used.

The HT IFC™ and the oligonucleotides, used together, allow the export of a plentitude of cDNA material barcoded (row by row) for individual cells (barcoded by exported pools) that can then be prepared in pools for use on a second generation sequencing platform or otherwise analyzed In the version illustrated herein, the HT IFC™ plus companion chemistry increases the number of cells that can be queried on a single chip more than 8-fold compared to the best currently available throughput, while at the same time significantly reducing the number of library preparation reactions from a potential 800 single reactions off-chip to only 20.

What is claimed is:

1. A method of exposing cells from a population to at least two different reagents, wherein each cell is exposed to the reagents individually, or in groups of two of more, the method comprising:
   (a) distributing cells from the population to a plurality of capture sites in a microfluidic device so that a plurality of capture sites each comprises one or more cells;
   (b) providing one or more first reagent(s) to each capture site;
   (c) providing one or more second reagent(s) to each capture site, wherein the second reagent(s) is/are different from the first reagent(s) and is/are provided separately from the first reagent(s), and the one or more first reagent(s) and the one or more second reagent(s) are separately provided to each capture site after distributing the cells to the capture sites;
   (d) conducting a reaction, whereby the reaction products encode an item of capture site information;
   (e) recovering the reaction products; and
   (f) analyzing the reaction products, wherein such analysis permits the identification of particular reaction products as having been derived from a single cell or group of cells at a particular capture site.

2. A method of incorporating nucleic acid sequences into reaction products from a cell population, wherein the nucleic acid sequences are incorporated into the reaction products of each cell individually, or in groups of up to 1000, the method comprising:
   (a) distributing cells from the population to a plurality of capture sites in a microfluidic device so that a plurality of capture sites each comprises one or more cells;
   (b) providing one or more first reagent(s) to each capture site;
   (c) providing one or more second reagent(s) to each capture site, wherein the second reagent(s) is/are different from the first reagent(s) and is/are provided separately from the first reagent(s), and the one or more first reagent(s) and the one or more second reagent(s) are separately provided to each capture site after distributing the cells to the capture sites;
   (d) conducting a reaction in which nucleic acid sequences are incorporated into the reaction products of each cell or group of cells, individually;
   (e) recovering the reaction products; and
   (f) analyzing the reaction products, wherein such analysis permits the identification of particular reaction products as having been derived from a single cell or group of cells at a particular capture site.

3. A method of incorporating nucleic acid sequences into nucleic acids of a cell population, wherein the nucleic acid sequences are incorporated into the nucleic acids of each cell individually or in groups of up to 1000, the method comprising:
(a) distributing cells from the population to a plurality of capture sites in a microfluidic device so that a plurality of capture sites each comprises one or more cells;
(b) providing one or more first reagent(s) to each capture site;
(c) providing one or more second reagent(s) to each capture site, wherein the second reagent(s) is/are different from the first reagent(s) and is/are provided separately from the first reagent(s), and the one or more first reagent(s) and the one or more second reagent(s) are separately provided to each capture site after distributing the cells to the capture sites;
(d) conducting a reaction in which nucleic acid sequences are incorporated into the nucleic acids of each cell or group of cells, individually, to produce reaction products;
(e) recovering the reaction products; and
(f) analyzing the reaction products, wherein such analysis permits the identification of particular reaction products as having been derived from a single cell or group of cells at a particular capture site.

4. The method of claim 1, where the distribution is carried out so that a plurality of capture sites each comprise not more than a single cell.

5. The method of claim 1, wherein the reaction incorporates a nucleotide barcode into the reaction products.

6. The method of claim 5, wherein the barcode encodes an item of capture site information.

7. The method of claim 1, wherein the reaction incorporates a nucleic acid sequence that uniquely identifies the molecule into which it is incorporated.

8. The method of claim 3, wherein the reaction comprises reverse transcription of RNA.

9. The method of claim 8, wherein the first reagent(s) comprise a reverse transcription (RT) primer comprising a poly-dT sequence and a first barcode 5' of the poly-dT sequence.

10. The method of claim 9, wherein the RT primer additionally comprises a first unique molecular index (UMI).

11. The method of claim 10, wherein the first UMI is 5' of the poly-dT sequence.

12. The method of claim 9, wherein the RT primer additionally comprises a first linker.

13. The method of claim 12, wherein the first linker is at the 5' end of the RT primer.

14. The method of claim 9, wherein the RT primer additionally comprises an anchor sequence 3' of the poly-dT sequence.

15. The method of claim 8, wherein the reaction additionally comprises second-strand synthesis to produce cDNA.

16. The method of claim 8, wherein the second reagent(s) comprise a 5' oligonucleotide comprising a poly-riboG sequence.

17. The method of claim 16, wherein the 5' oligonucleotide comprises a second barcode 5' of the poly-riboG sequence.

18. The method of claim 16, wherein the 5' oligonucleotide additionally comprises a second UMI.

19. The method of claim 18, wherein the second UMI is 5' of the poly-riboG sequence.

20. The method of claim 16, wherein the 5' oligonucleotide additionally comprises a second linker.

21. The method of claim 20, wherein the second linker is at the 5' end of the 5' oligonucleotide.

22. The method of claim 21, wherein the method comprises producing cDNA, wherein one strand has the structure: 5'-second linker-nucleotide sequence derived from RNA-first linker-3', with a barcode located in between the linkers.

23. The method of claim 22, wherein the first barcode is located adjacent to the first linker.

24. The method of claim 23, wherein the second barcode is located adjacent to the second linker.

25. The method of claim 23, wherein said one strand of cDNA has the structure: 3'-second linker-poly dC-nucleotide sequence derived from RNA-first barcode-first linker-5'.

26. The method of claim 25, wherein said one strand of cDNA has the structure: 3'-second linker-second barcode-poly dC-nucleotide sequence derived from RNA-first barcode-first linker-5'.

27. The method of claim 25, wherein said one strand of cDNA has a structure selected from the group consisting of:
3'-second linker-poly dC-nucleotide sequence derived from RNA-first UMI-first barcode-first linker-5'; and
3'-second linker-poly dC-nucleotide sequence derived from RNA- first barcode-first UMI-first linker-5'.

28. The method of claim 27, wherein said one strand of cDNA has a structure selected from the group consisting of:
3'-second linker-second barcode-second UMI-poly dC-nucleotide sequence derived from RNA-first UMI-first barcode-first linker-5';
3'-second linker-second barcode- second UMI-poly dC-nucleotide sequence derived from RNA- first barcode-first UMI-first linker-5';
3'-second linker- second UMI-second barcode-poly dC-nucleotide sequence derived from RNA-first UMI-first barcode-first linker-5'; and
3'-second linker- second UMI-second barcode-poly dC-nucleotide sequence derived from RNA- first barcode-first UMI-first linker-5'.

29. The method of claim 3, wherein the reaction comprises amplification of DNA.

30. The method of claim 29, wherein the first and/or second reagent(s) comprise first and/or second amplification primers, respectively, wherein the first and/or second amplification primers comprise a first or second barcode, respectively, that is 5' of a primer sequence.

31. The method of claim 30, wherein the first and/or second amplification primers additionally comprise a first or second UMI, respectively.

32. The method of claim 31, wherein the first or second UMI is 5' of the primer sequence.

33. The method claim 30, wherein the first and/or second amplification primer additionally comprises a first or second linker.

34. The method of claim 33, wherein the first or second linker is at the 5' end of the amplification primer.

35. The method of claim 34, wherein the method comprises producing amplicons, wherein one strand has the structure: 5'-second linker-nucleotide sequence derived from cellular DNA-first linker-3', with a barcode located in between the linkers.

36. The method of claim 35, wherein one strand has the structure: 3'-second linker-nucleotide sequence derived from cellular DNA-first barcode-first linker-5'.

37. The method of claim 25, wherein said one strand has the structure:

3'-second linker-second barcode- nucleotide sequence derived from cellular DNA-first barcode-first linker-5'.

38. The method of claim 25, wherein said one strand has a structure selected from the group consisting of:
3'-second linker-nucleotide sequence derived from cellular DNA-first UMI-first barcode-first linker-5'; and
3'-second linker- nucleotide sequence derived from cellular DNA- first barcode-first UMI-first linker-5'.

39. The method of claim 27, wherein said one strand has a structure selected from the group consisting of:
3'-second linker-second barcode-second UMI- nucleotide sequence derived from cellular DNA-first UMI-first barcode-first linker-5';
3'-second linker-second barcode- second UMI- nucleotide sequence derived from cellular DNA- first barcode-first UMI-first linker-5';
3'-second linker- second UMI-second barcode- nucleotide sequence derived from cellular DNA-first UMI-first barcode-first linker-5'; and
3'-second linker- second UMI-second barcode-poly dC-nucleotide sequence derived from cellular DNA- first barcode- first UMI-first linker-5'.

40. The method of claim 1, wherein the microfluidic device comprises a matrix-type microfluidic device comprising:
capture sites arranged in a matrix of R rows and C columns, wherein R and C are integers greater than 1, and wherein the capture sites can be fluidically isolated from one another after distribution of cells to the capture sites;
a set of R first input lines configured to deliver the first reagent(s) to capture sites in a particular row;
a set of C second input lines configured to deliver second reagent(s) to capture sites in a particular column, wherein said delivery is separate from the delivery first reagent(s), wherein, after the reaction, reaction products are recovered from the microfluidic device in pools of reaction products from individual rows or columns.

41. The method of claim 40, wherein an RT primer is delivered to capture sites via one set of the input lines, and a 5' oligonucleotide is delivered to the capture sites via the other set of input lines.

42. The method of claim 40, wherein a first amplification primer is delivered to capture sites via one set of the input lines, and a second amplification primer is delivered to the capture sites via the other set of input lines.

43. The method of claim 1, wherein all methods steps are performed in the microfluidic device.

44. The method of claim 20, wherein the reaction products are subjected to preamplification using linker primers that anneal to the first and second linkers, wherein the linker primers are the same or different.

45. The method of claim 44, wherein said preamplification is performed in the microfluidic device.

46. The method of claim 1, wherein the reaction products are subjected to tagmentation.

47. The method of claim 1, wherein the reaction incorporates one or more DNA sequencing primer binding sites into the reaction products.

48. The method of claim 1, wherein the reaction products are subjected to DNA sequencing.

49. The method of claim 48, wherein the sequences obtained from DNA sequencing are identified as having been derived from a particular capture site based on one or two barcodes.

50. The method of claim 40, wherein the pools of reaction products are separately subjected to preamplification using linker primers that anneal to the first and second linkers, wherein the linker primers are the same or different.

51. The method of claim 40, wherein the exported pools of reaction products are combined into one reaction mixture, which is subjected to preamplification using linker primers that anneal to the first and second linkers, wherein the linker primers are the same or different.

52. The method of claim 40, wherein the microfluidic device is sufficiently transparent on at least one surface to permit visualization of cells and/or, when a visualizable label is employed, signals associated with cells or reaction products.

53. The method of claim 52, additionally comprising imaging the cell-occupied capture sites before conducting the reaction.

54. The method of claim 1, wherein the reaction comprises whole transcriptome amplification (WTA), whole genome amplification (WGA), protein proximity ligation, microRNA (mRNA) preamplification, target-specific amplification of RNA or DNA.

55. The method of claim 1, wherein the microfluidic device comprises at least 750 capture sites.

56. The method of claim 1, where the one or more first reagent(s) and the one or more second reagent(s) are provided to a pair of fluidically isolatable chambers in the capture site that are distinct from one another and distinct from a chamber including the capture feature.

* * * * *

UNITED STATES PATENT AND TRADEMARK OFFICE
CERTIFICATE OF CORRECTION

PATENT NO. : 10,190,163 B2
APPLICATION NO. : 15/055252
DATED : January 29, 2019
INVENTOR(S) : Carolyn G. Conant et al.

It is certified that error appears in the above-identified patent and that said Letters Patent is hereby corrected as shown below:

In the Claims

Claim 51 (Column 30, Line 23) delete the word "exported".

Signed and Sealed this
Fifth Day of May, 2020

Andrei Iancu
*Director of the United States Patent and Trademark Office*